(12) United States Patent
Parng et al.

(10) Patent No.: US 8,216,516 B2
(45) Date of Patent: Jul. 10, 2012

(54) ANALYTICAL SYSTEM, ANALYTICAL METHOD AND FLOW-PATH STRUCTURE

(75) Inventors: Shaw-Hwa Parng, Kaohsiung County (TW); Chung-Hsien Tsai, Taipei County (TW); Fu-Chun Huang, Taipei County (TW); Chih-Wen Yang, Taoyuan County (TW)

(73) Assignee: Industrial Technology Research Institute, Hsinchu (TW)

( * ) Notice: Subject to any disclaimer, the term of this patent is extended or adjusted under 35 U.S.C. 154(b) by 399 days.

(21) Appl. No.: 12/634,362

(22) Filed: Dec. 9, 2009

(65) Prior Publication Data

US 2011/0053202 A1 Mar. 3, 2011

(30) Foreign Application Priority Data

Aug. 25, 2009 (TW) ................. 98128475 A

(51) Int. Cl.
*G01N 33/00* (2006.01)
(52) U.S. Cl. ......... 422/72; 422/68.1; 422/501; 422/533; 422/548
(58) Field of Classification Search ................. 422/68.1, 422/501, 533, 548
See application file for complete search history.

(56) References Cited

U.S. PATENT DOCUMENTS

| | | | |
|---|---|---|---|
| 5,061,381 A | 10/1991 | Burd | |
| 5,089,417 A | 2/1992 | Wogoman | |
| 5,110,724 A | 5/1992 | Hewett | |
| 5,242,606 A | 9/1993 | Braynin et al. | |
| 6,548,788 B2 | 4/2003 | Kellogg et al. | |
| 2007/0277596 A1 | 12/2007 | Kim et al. | |

FOREIGN PATENT DOCUMENTS

| | | |
|---|---|---|
| CN | 1975434 | 6/2007 |
| CN | 101252994 | 4/2011 |
| TW | I324685 | 5/2010 |

OTHER PUBLICATIONS

Taiwan Patent Office, Notice of Allowance, Patent Application Serial No. 98128475, Jan. 31, 2012, Taiwan.

*Primary Examiner* — Sam P Siefke

(57) ABSTRACT

An analytical system for performing centrifugal analysis on a working fluid with different components includes a uniform-dividing unit with a reduced cross section to divide the working fluid, a separating unit connected to the uniform-dividing unit, and a detecting unit. The detecting unit includes a detection compartment and a constant-quantity region connected to the separating unit through a separation channel. When rotating the uniform-dividing unit, the working fluid located at the uniform-dividing unit is transmitted to and separated by the separating unit, thereby causing one component of the working fluid to be separated from the other component and transmitted to the detection compartment through the constant-quantity region. With constant-quantity region, the detection compartment can be prevented from flushing by the excess of the separated component, and thus yield of product detection can be increased and different assays detection is carried out with a small sample volume at the same time.

57 Claims, 18 Drawing Sheets

ANALYTICAL SYSTEM, ANALYTICAL METHOD AND FLOW-PATH STRUCTURE

CROSS REFERENCE TO RELATED APPLICATIONS

This Application claims priority of Taiwan Patent Application No. 098128475, filed on Aug. 25, 2009, the entirety of which is incorporated by reference herein.

BACKGROUND OF THE INVENTION

1. Field of the Invention

The present invention relates to an analytical system, analytical method and a flow-path structure thereof capable of performing separation of a sample or a working fluid comprising different components with different characteristics by a uniform division process including centrifugal and capillary forces. The sample or the working fluid serves as a carrier for biochemical detection. Particularly, the present invention relates to an analytical system, analytical method and a flow-path structure thereof capable of performing separation of a sample or a working fluid comprising different components with different characteristics by using a uniform dividing compartment with varied geometrical shapes having gradually-increasing flow resistances, eliminating interference of a sample injection error using buffering compartments, separating substances or components with different specific gravities using a sinking chamber of a collecting compartment, adjusting excess working fluid using an overflowing compartment and metering the working fluid using a constant-quantity detection compartment, thereby increasing biochemical detection yield.

2. Description of the Related Art

In general, a conventional fluid separation device has a complicated structure. U.S. Pat. No. 6,548,788, for example, discloses methods and an apparatus for performing microanalytic and microsynthetic analyses and procedures. The fluid separation apparatus comprises a microchannel to control the movement of fluid. However, the microchannel must be manufactured by micromachining technology. Thus, when compared with plastic injection technology, the cost of the fluid separation apparatus is high.

U.S. Pat. Nos. 5,061,381 and 5,089,417 also disclose fluid separation devices having complicated structures and high manufacturing costs.

For separating blood cells, conventional blood detection methods are roughly classified into membrane-filtering methods and fluidic chip methods. The advantage of the membrane-filtering method is that it is simplistic. For example, U.S. Pat. No. 5,110,724 discloses an assay device utilizing membranes to separate blood cells and guide plasma into a reaction display region. However, due to biochemical reaction limitations, subsequent operations and tests on blood cells related to immune analysis cannot be performed. For the fluidic chip method, the process is complicated. The fluidic chip method comprises sample constant-quantity, dilution, mixing, centrifugal, distributing and detection processes. For example, U.S. Pat. No. 5,242,606 discloses a fluid separation device having a method comprising sample injection, diluted solution mixing, centrifugal, and distribution and constant-quantity detection processes. However, the process gets more complex and the number of required samples increases when the size of the chip increases. Moreover, the volume of the injected blood in comparison with the actual sampled blood changes due to blood remaining in the injector caused by viscosity. For example, the volume of the blood to be sampled by the injector may be 100 μL and the actual volume of the blood injected into the chip may be 98 μL. Thus, 2 μL of blood is left on the walls of the injector, injection regions and outside of the micro flow structure, thereby causing an insufficient volume of the blood to be injected into the microchannels. Additionally, actual volume of the injected fluid is influenced by human error when the injector is manually operated or by hands.

BRIEF SUMMARY OF THE INVENTION

The invention provides a flow-path structure for performing centrifugal separation of a working fluid comprising at least one first component and at least one second component with different characteristics therebetween. The flow-path structure comprises an injection compartment, a uniform dividing compartment, a collecting compartment, a detection compartment and a separation channel. The injection compartment is utilized for receiving the working fluid to be injected. The uniform dividing compartment, connected to the injection compartment relative to a reference position to divide the working fluid transmitted from the injection compartment, comprises a section gradually reduced away from the reference position. The collecting compartment, connected to the uniform dividing compartment, comprises a plurality of collecting regions connected to each other. The separation channel is utilized to connect one of the collecting regions to the detection compartment. When the uniform dividing compartment is rotated relative to the reference position, the working fluid located in the uniform dividing compartment is transmitted to the collecting regions of the collecting compartment, and the at least one first component and the at least one second component of the working fluid are centrifugally separated from each other by the collecting regions of the collecting compartment. When the rotating uniform dividing compartment is stopped relative to the reference position, the at least one first component of the working fluid located at the collecting regions of the collecting compartment is transmitted to the separation channel, and when the uniform dividing compartment that was stopped begins to rotate relative to the reference position, the at least one first component of the working fluid located at the separation channel is centrifugally transmitted to the detection compartment through the separation channel, so that the at least one first component is completely separated from the at least one second component.

Additionally, the invention provides an analytical system capable of analyzing a working fluid comprising at least one first component and at least one second component with different characteristics therebetween. The analytical system comprises a uniform dividing unit, a separation unit and a detection unit. The uniform dividing unit comprises a plurality of uniform dividing compartments utilized to uniformly divide the working fluid and to be rotated relative to a reference position, wherein each of the uniform dividing compartments comprises a section gradually reduced away from the reference position. The separation unit comprises a plurality of collecting compartments respectively connected to the uniform dividing compartments of the uniform dividing unit and a plurality of separation channels, wherein each of the collecting compartments comprises a plurality of collecting regions connected to each other. The detection unit comprises a plurality of detection compartments respectively connected to at least one of the collecting regions of each of the collecting compartments through the separation channels of the separation unit. When the uniform dividing compartments of the uniform dividing unit are rotated relative to the reference position, the working fluid located at the uniform dividing compartments of the uniform dividing unit is transmitted to the collecting regions of the collecting compartments of the separation unit, and the at least one first component and the at least one second component of the working fluid are centrifugally separated from each other by the collecting regions of the collecting compartments of the separation unit. When the rotating uniform dividing compartments of the uniform dividing unit are stopped relative to the reference position, the at least one first component of the working fluid located at the collecting regions of the collecting compartments of the separation unit is transmitted to the separation channels, and when the uniform dividing compartments of the uniform dividing unit those were stopped begin to rotate relative to the reference position, the at least one first component of the working fluid located at the separation channels of the separation unit is centrifugally transmitted to the detection compartments of the detection unit through the separation channels of the separation unit, so that the at least one first component is completely separated from the at least one second component.

The uniform dividing compartments of the uniform dividing unit comprise a similar droplet-like hollow structure formed with at least one slanted surface, respectively.

The uniform dividing unit further comprises a plurality of buffering compartments respectively connected between the uniform dividing compartments and the collecting compartments of the separation unit relative to the reference position, wherein each of the buffering compartments comprises a section gradually reduced away from the reference position. The buffering compartments of the uniform dividing unit comprise a similar droplet-like hollow structure, respectively. Each of the uniform dividing compartments of the uniform dividing unit, each of the buffering compartments of the uniform dividing unit, and each of the collecting compartments of the separation unit are arranged along a radial direction passing through the reference position.

The analytical system further comprises an overflowing unit comprising a plurality of overflowing compartments respectively connected to the collecting compartments of the separation unit. When the overflowing compartments of the overflowing unit are rotated relative to the reference position, excess working fluid injected to the collecting compartments of the separation unit is transmitted to the overflowing compartments of the overflowing unit.

Each of the detection compartments of the detection unit comprises a detecting region and a first constant-quantity region connected between each of the separation channels of the separation unit and the detecting region. When the rotating uniform dividing compartments of the uniform dividing unit is stopped relative to the reference position, the at least one first component of the working fluid located at the collecting regions of the collecting compartments of the separation unit is transmitted to the separation channels of the separation unit, and when the uniform dividing compartments of the uniform dividing unit those were stopped begin to rotate relative to the reference position, the at least one first component of the working fluid located at the separation channels of the separation unit is centrifugally transmitted to the detecting regions of the detection compartments of the detection unit through the separation channels of the separation unit and the first constant-quantity regions of the detection compartments of the detection unit, so that the at least one first component is completely separated from the at least one second component. The first constant-quantity regions of the detection compartments of the detection unit comprise a plurality of recesses.

The analytical system further comprises an exhaust unit comprising a plurality of exhaust compartments, wherein each of the detection compartments of the detection unit comprises a detecting region and a second constant-quantity region connected between the detecting region and each of the exhaust compartments of the exhaust unit. The second constant-quantity regions of the detection compartment of the detection unit comprise a plurality of recesses.

The analytical system further comprises an exhaust unit comprising a plurality of exhaust compartments respectively connected to the collecting compartments of the separation unit and the detection compartment of the detection unit.

The analytical system further comprises a main board comprising a base surface, wherein each of the collecting regions of the collecting compartments of the separation unit comprise a first collecting region, a second collecting region and a third collecting region which are formed with different depths from each other, the second collecting region is connected between the first collecting region and the third collecting region, and the second collecting region has a depth ranged between a depth of the first collecting region and a depth of the third collecting region relative to the base surface of the main board. A sectional difference of the depth of the first collecting region and the depth of the second collecting region is different from a sectional difference of the depth of the second collecting region and the depth of the third collecting region relative to the base surface of the main board.

Each of the collecting compartments of the separation unit further comprises a slanted surface disposed between the first collecting region and the second collecting region relative to the base surface of the main board.

Each of the third collecting regions of the collecting compartments of the separation unit comprises a similar L-shaped chamber formed with an opening connected to the second collecting region.

The analytical system further comprises a main board comprising a base surface, an overflowing unit comprising a plurality of overflowing compartments respectively connected to the collecting compartments of the separation unit, an exhaust unit comprising a plurality of exhaust compartments respectively connected to the detection compartments of the detection unit. Also, the analytical system further comprises an injection unit comprising an injection compartment connected to the uniform dividing compartments of the uniform dividing unit to receive the working fluid to be injected. The uniform dividing unit further comprises a plurality of buffering compartments, the collecting regions of each of the collecting compartments of the separation unit comprise a first collecting region, a second collecting region and a third collecting region which are formed with different depths from each other, the second collecting region is connected between the first collecting region and the third collecting region, and the buffering compartments of the uniform dividing unit are respectively connected between the uniform dividing compartment of the uniform dividing unit and the collecting compartment of the separation unit relative to the reference position. The uniform dividing compartments and the buffering compartments of the uniform dividing unit, the overflowing compartments of the overflowing unit, the detection compartments of the detection unit, the exhaust compartments of the exhaust unit, and the first, second and third collecting regions of the collecting compartments of the separation unit are slots formed on the base surface of the main board. The depths of the second collecting regions of the collecting compartments of the separation unit and the depths of the separation channels of the separation unit are relatively less than the depths of the injection compartment of the injection unit, the uniform dividing compartments and the buffering compartments of the uniform dividing unit, the overflowing compartments of the overflowing unit, and the first and third collecting regions of the collecting compartments of the separation unit.

The working fluid located at the uniform dividing compartments of the uniform dividing unit is transmitted to the collecting compartment at a first predetermined time period when the uniform dividing compartments of the uniform dividing unit is rotated relative to the reference position, and the separation of the at least one first and second components of the working fluid located at the collecting regions of the collecting compartments of the separation unit is performed at a second predetermined time period, wherein the first predetermined time period is prior to the second predetermined time period, and the collecting regions of the collecting compartments of the separation unit are filled with the separated first component. The at least one first component of the working fluid located at the collecting regions of the collecting compartments of the separation unit is transmitted to the separation channels of the separation unit when the rotating uniform dividing compartments of the uniform dividing unit is stopped relative to the reference position, and the separated at least one first component located at the separation channels of the separation unit is centrifugally transmitted to the detection compartment through the separation channels of the separation unit by an acting force when the uniform dividing compartments of the uniform dividing unit that was stopped begins to rotate relative to the reference position, so that the at least one first component is completely separated from the at least one second component. The acting force comprises a Coriolis force generated by Coriolis acceleration.

The working fluid is moved by an accelerated motion in the first predetermined time period relative to the reference position, and the working fluid is moved by a uniform velocity motion in the second predetermined time period relative to the reference position.

Each of the uniform dividing compartments of the uniform dividing unit and each of the collecting compartments of the separation unit are arranged along a radial direction relative to the reference position. The uniform dividing unit and the separation unit are rotated about a reference axis at which the reference position is located.

Each of the separation channels of the separation unit comprises at least one segment connected to at least one of the collecting regions of the collecting compartments of the separation unit. Also, an oblique angle formed between an extending direction of the at least one segment of the separation channel and an extending direction of the at least one of the collecting regions of the collecting compartments of the separation unit is not greater than 30 degrees. Each of the separation channels of the separation unit comprises a first segment obliquely connected to the at least one of the collecting regions of the collecting compartments of the separation unit, a second segment, and a third segment connected to the detection compartment, wherein the second segment is connected between the first segment and the third segment, a first angle formed between the first segment and the second segment is not less than 90 degrees, and a second angle formed between the second segment and the third segment is not less than 90 degrees.

A specific gravity of the at least one first component is different from that of the at least one second component.

The analytical system further comprises a controlling unit and an injection unit comprising an injection compartment connected to the uniform dividing compartments of the uniform dividing unit to receive the working fluid to be injected, wherein the working fluid injected into the injection compartment of the injection unit is controlled by the controlling unit.

The analytical system further comprises a plurality of objects with a first marked substance, disposed in the uniform dividing compartments of the uniform dividing unit, wherein the working fluid further comprises a second marked substance capable of bonding to the first marked substance of the objects. The objects comprise glass balls, magnetic balls or other carriers. The first marked substance comprises a conjunctive DNA or RNA, a protein, a biomarker, an antibody, a cell, or other biomolecular, and the second marked substance comprises a markable complementary DNA or RNA, a substrate, an enzyme, a coenzyme, a complement, an antigen, other cells or biomolecular.

The invention further provides an analytical method, comprising the steps of: providing a working fluid comprising at least one first component and at least one second component with different characteristics; providing a flow-path structure with an injection compartment, a uniform dividing compartment connected to the injection compartment and formed with a gradually-reduced section, a buffering compartment connected to the uniform dividing compartment and formed with a gradually-reduced section, a collecting compartment connected to the uniform dividing compartment and comprising a plurality of collecting regions which are connected to each other and formed with different depths, a separation channel connected to one of the collecting regions of the collecting compartment, and a detection compartment connected to the separation channel; injecting the working fluid into the injection compartment of the flow-path structure; uniformly dividing the working fluid from the injection compartment by the uniform dividing compartment and the buffering compartment to limit the uniformly divided working fluid from entering the collecting regions of the collecting compartment; rotating the flow-path structure to cause the working fluid located in the uniform dividing compartment and the buffering compartment entering the collecting compartment, so that the at least one first component and the at least one second component of the working fluid are centrifugally separated from each other by the collecting regions of the collecting compartment; stopping the rotation of the flow-path structure to transmit the at least one first component of the working fluid located at the collecting regions of the collecting compartment toward the detection compartment through the separation channel; and driving the flow-path structure that was stopped to rotate for transmitting the separated at least one first component to the detection compartment through the separation channel, so that the at least one first component is completely separated from the at least one second component.

Additionally, the analytical method further provides the following steps: providing a plurality of objects with a first marked substance and the working fluid with a second marked substance; and selectively disposing the objects with the first marked substance in one of the uniform dividing compartment or the buffering compartment, so that the working fluid injected into the uniform dividing compartment or the buffering compartment is capable of bonding to the first marked substance of the objects.

A detailed description is given in the following embodiments with reference to the accompanying drawings.

BRIEF DESCRIPTION OF THE DRAWINGS

The present invention can be more fully understood by reading the subsequent detailed description and examples with references made to the accompanying drawings, wherein.

DETAILED DESCRIPTION OF THE INVENTION

The following description is made for the purpose of illustrating the general principles of the invention and should not be taken in a limiting sense. The scope of the invention is best determined by reference to the appended claims.

Figure 1A:
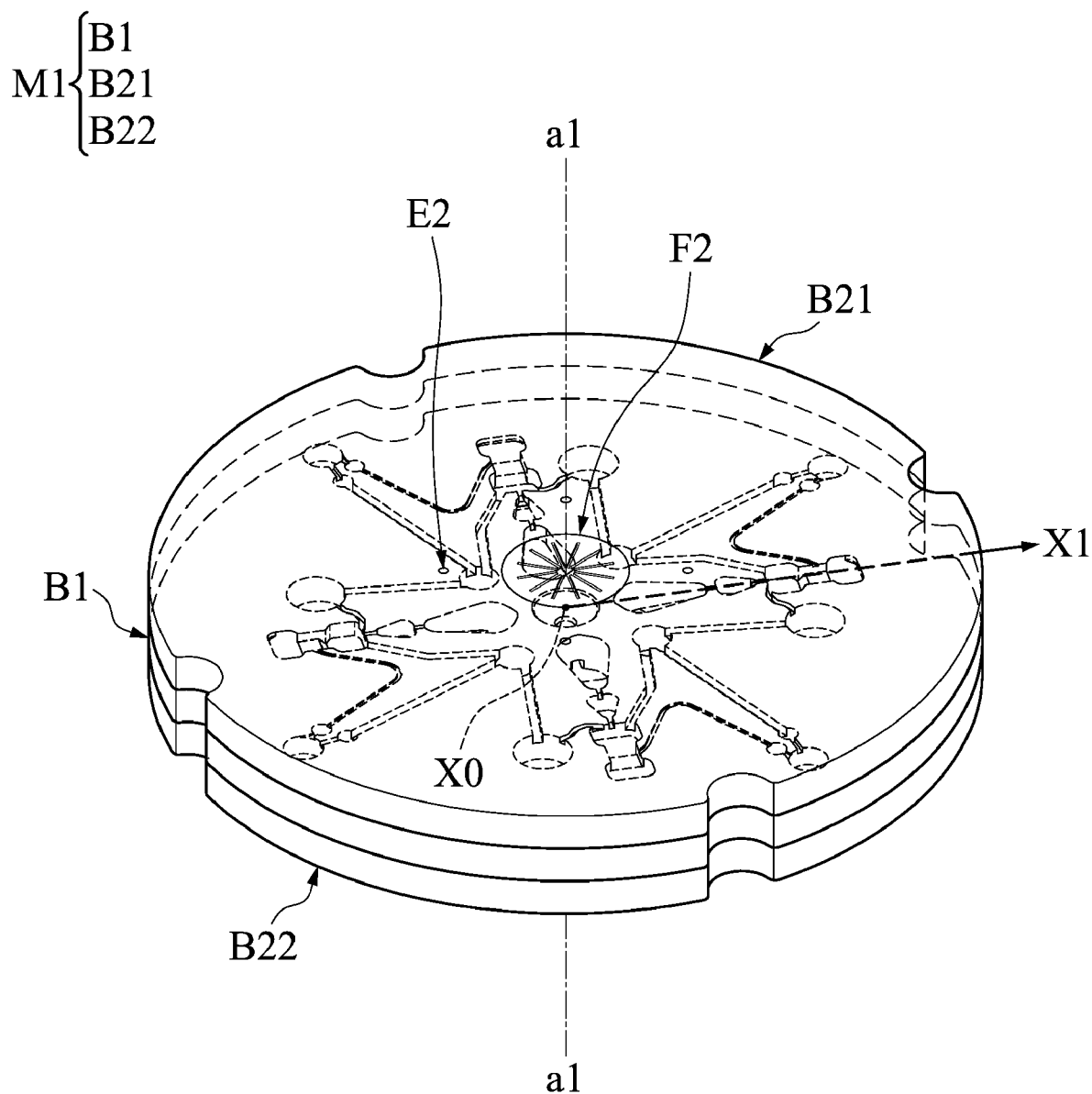
FIG. 1A is a perspective view of a flow-path structure of a first embodiment of the invention.
Figure 1B:
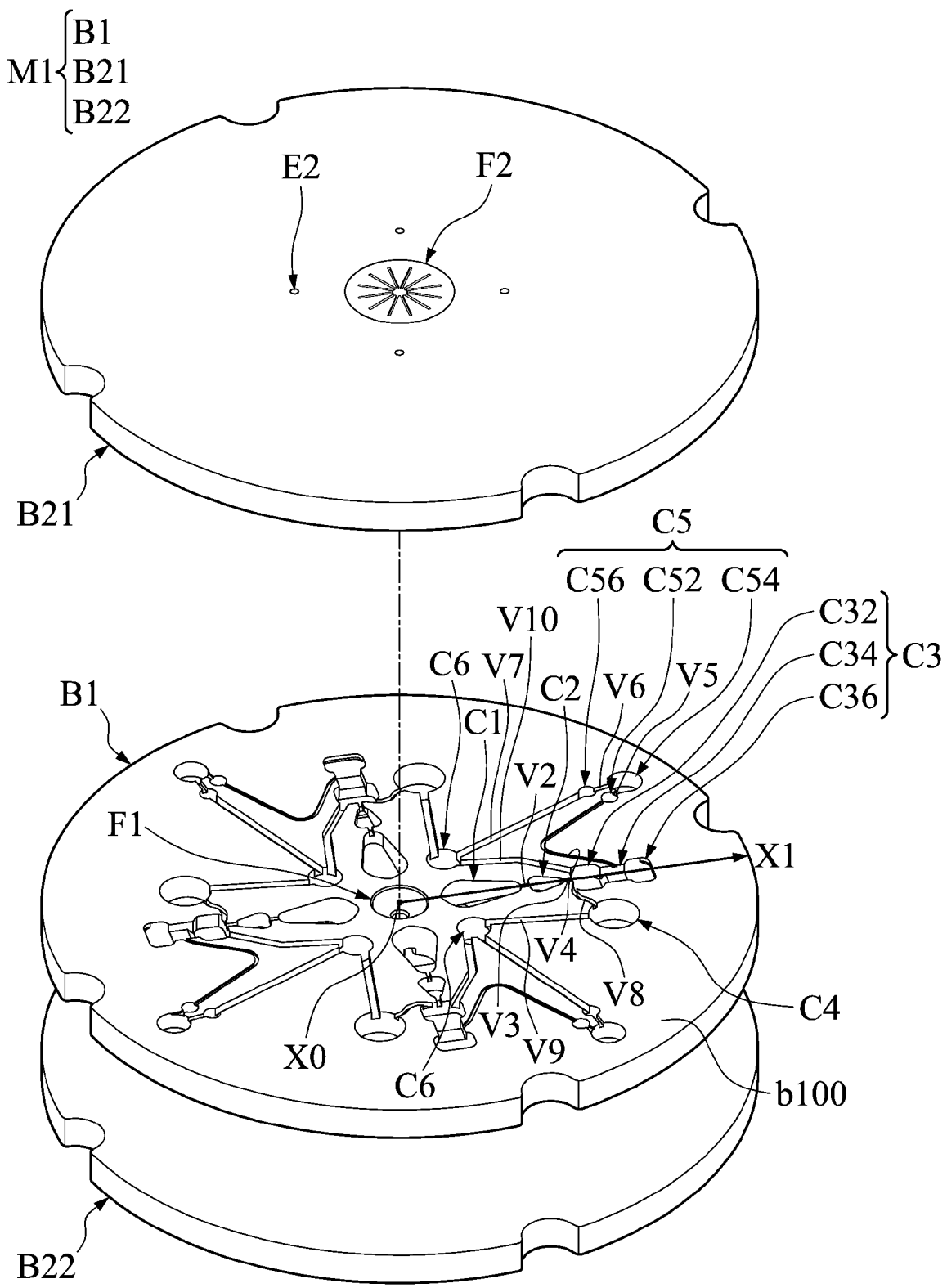
FIG. 1B is an exploded view of the flow-path structure of FIG. 1A.
Figure 1C:
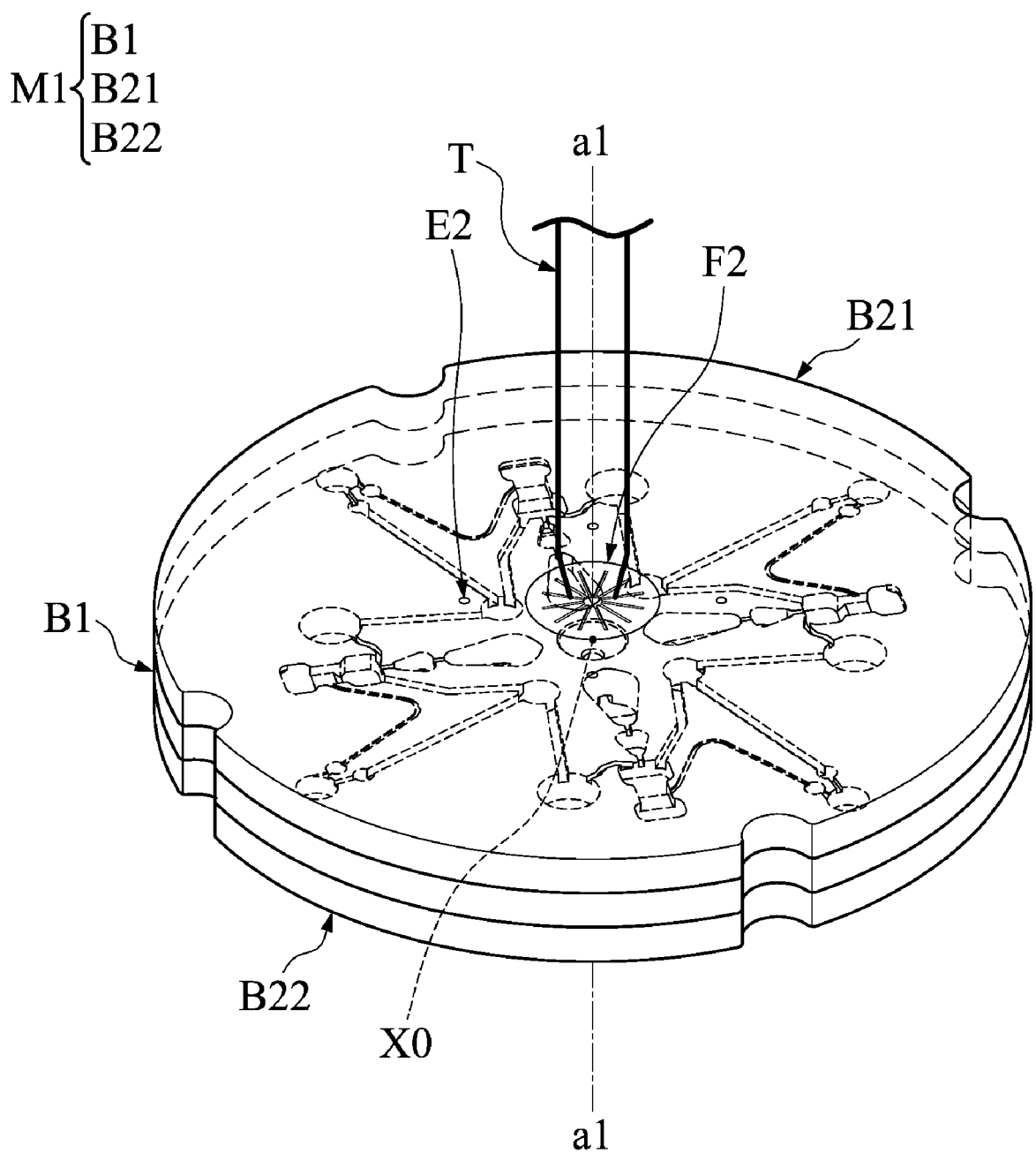
FIG. 1C is a perspective view of an injector being inserted into the flow-path structure of FIG. 1A.

FIG. 1A is a perspective view of a flow-path structure M1 of a first embodiment, FIG. 1B is an exploded view of the flow-path structure M1 of FIG. 1A, and FIG. 1C is a perspective view of an injector T (e.g., pipette) being inserted into the flow-path structure M1 of FIG. 1A.

The flow-path structure M1 comprises a main board B1, a first cover plate (or an upper cover plate) B21, and a second cover plate (or a lower cover plate) B22. The main board B1 configured with flow paths is disposed between the first cover plate B21 and the second cover plate B22, and the flow paths of the main board B1 is covered by the first cover plate B21, so that a closed space is formed on the main board B1 covered by the first and second cover plates B21 and B22. The first cover plate B21 is a disc-like structure providing an injection-hole cover pad F2 and several exhaust holes E2. The injection-hole cover pad F2 is an elastic structure for piercing and is capable of elastically recovering when being pierced. The main board B1 is a disc-like structure providing a base surface (b100), an injection compartment F1, and a plurality of flow paths B1.

In FIG. 1C, when the injector T, absorbed with a working fluid K (e.g., a blood, a sample or a working fluid) comprising a first component k01 and a second component k02 with different characteristics (e.g. specific gravities), is inserted into the injection-hole cover pad F2 of the first cover plate B21, the injector T is properly positioned by piercing the injection-hole cover pad F2 of the first cover plate B21 to inject the working fluid K into the injection compartment F1 and the plurality of flow paths B1 of the main board B1. When the injector T is separated from the injection-hole cover pad F2 of the first cover plate B21, the injection compartment F1 is sealed by the recovered injection-hole cover pad F2 to prevent accidental sputtering of the working fluid K from the plurality of flow paths B1 of the main board B1 during the subsequent separation processes. In this embodiment, the first and second cover plates B21 and B22 are membranes utilized to bond to the main board B1 by packaging. The flow-path structure M1 of the embodiment is capable of performing uniform division and separation of the working fluid K comprising several components with different characteristics (e.g. specific gravities), thereby performing analysis and detection of the working fluid K.

Figure 2:
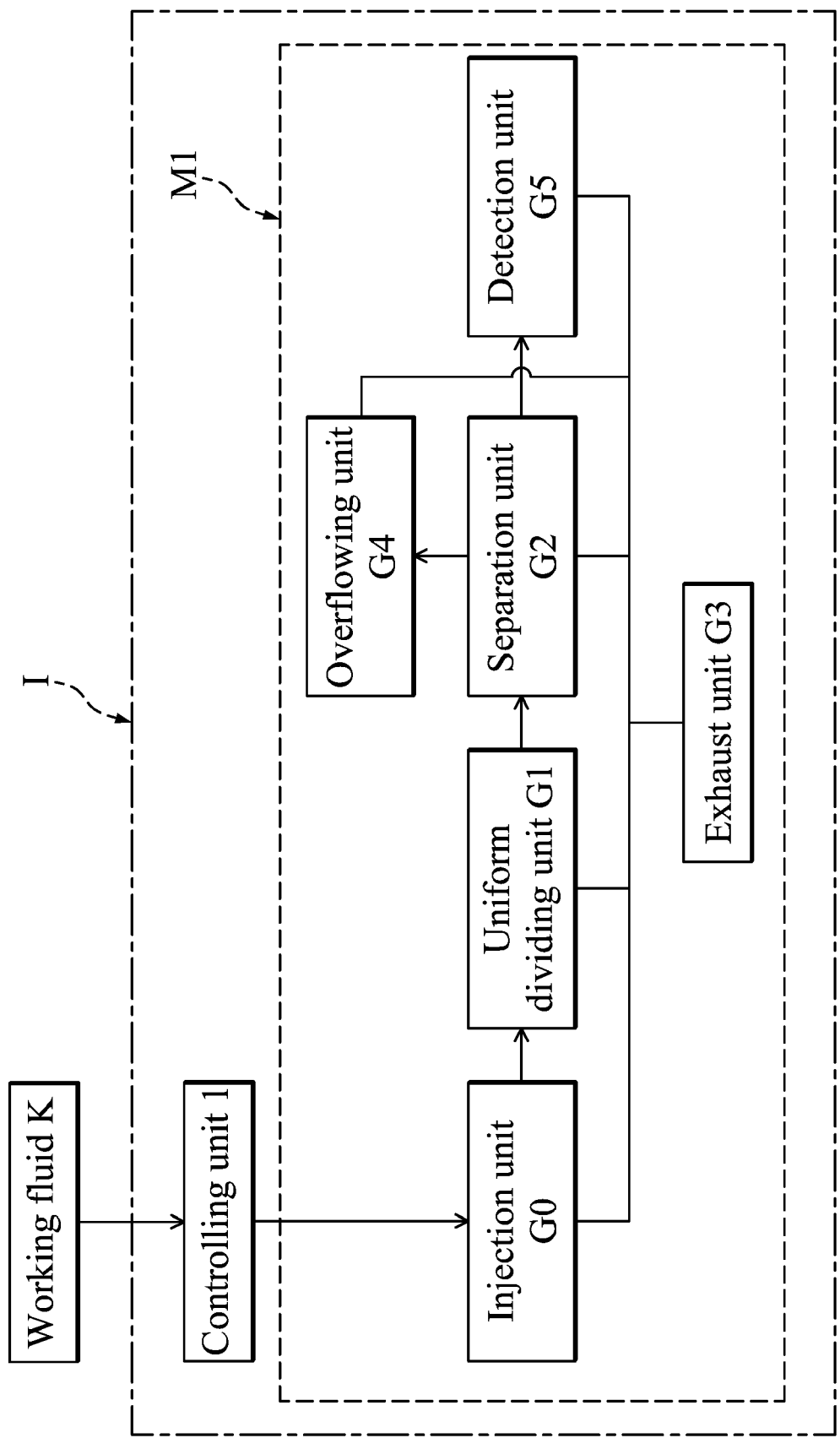
FIG. 2 is a block diagram of an analytical system of the invention.
Figure 3A:
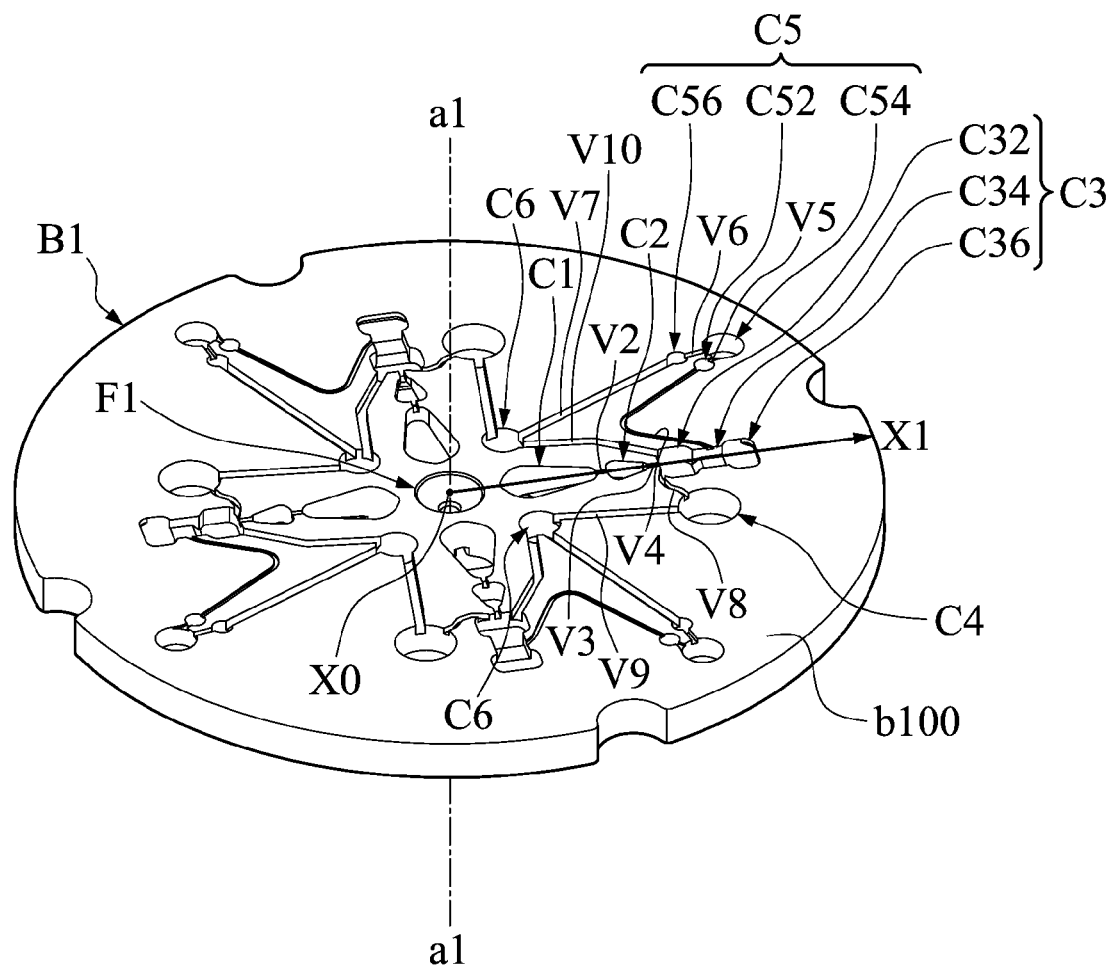
FIG. 3A is a perspective view of a main board of the flow-path structure in FIG. 1B.
Figure 3B:
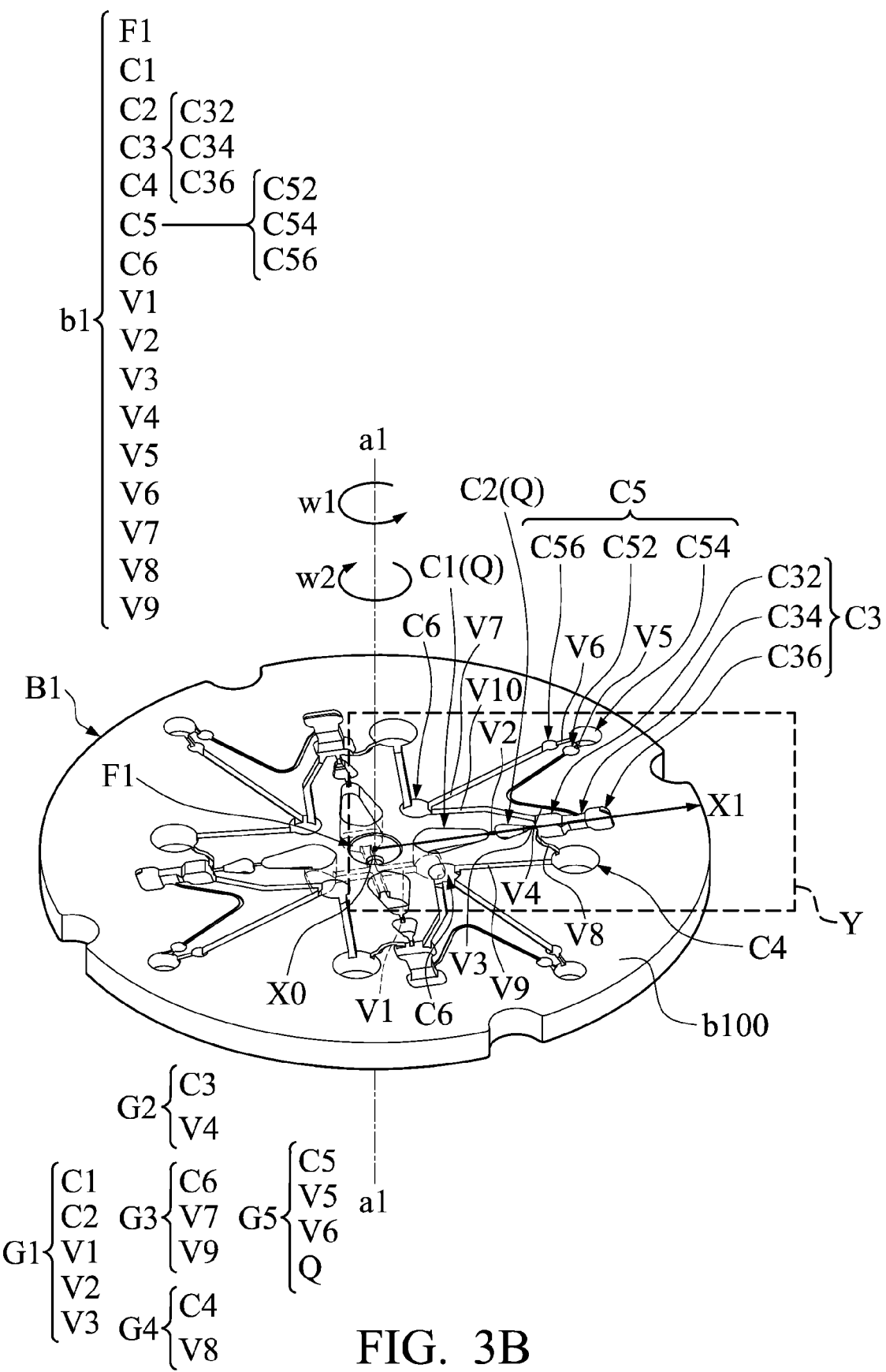
FIG. 3B is another perspective view of a main board of the flow-path structure in FIG. 1B.

FIG. 2 is a block diagram of an analytical system I, and FIGS. 3A and 3B are perspective views of the main board B1 of the flow-path structure M1 in FIG. 1B.

In FIG. 2, the analytical system I mainly comprises the flow-path structure M1 and a controlling unit 1 (e.g., a controller or computer provided with processor). With an adequate injector (not shown in FIGs.), the flow rate and flow speed of the working fluid K transmitted to the flow-path structure M1 can be automatically controlled by the controlling unit 1. The flow-path structure M1 mainly comprises an injection unit G0, a uniform dividing unit G1, a separation unit G2, an exhaust unit G3, an overflowing unit G4 and a detection unit G5.

In FIGS. 3A and 3B, the injection compartment F1 and the plurality of flow paths B1 are commonly disposed on the base surface b100 of the main board B1, and the injection compartment F1 is connected to the plurality of flow paths B1. A reference axis a1-a1 with a reference position X0 thereon is utilized to define the location of the injection compartment F1. The equally-spanned, radially-arranged and symmetrical flow paths B1 are respectively distributed along the radial directions X1, regarding the reference position X0 of the reference axis a1-a1 as a center thereof. The main board B1 can be relatively rotated along a first or second direction relative to the reference position X0 of the reference axis a1-a1. In this embodiment, the flow paths B1 have the same structure, the amount of the plurality of flow paths B1 are four, and the reference position X0 is a reference point. Although the injection compartment F1 and the four flow paths B1 are commonly disposed on the same plane, i.e., the base surface b100 of the main board B1, they are not limited thereto. The location and amount of the injection compartments F1 and the plurality of flow paths B1 can have various modifications and arrangements, as long as the uniform division and separation of the working fluid can be achieved. To briefly describe the structure of the main board B1, a single flow path b1 is utilized.

In FIG. 3B, the flow path B1 comprises the injection compartment F1, a uniform dividing compartment C1, a buffering compartment C2, a collecting compartment C3, an overflowing compartment C4, a detection compartment C5, an exhaust compartment C6, a first channel V1, a second channel V2, a third channel V3, a separation channel V4, a first constant-quantity channel V5, a second constant-quantity channel V6, a first exhaust channel V7, an overflow channel V8, a second exhaust channel V9 and a third exhaust channel V10. The buffering compartment C2, the collecting compartment C3, the overflowing compartment C4, the detection compartment C5, the exhaust compartment C6, the first channel V1, the second channel V2, the third channel V3, the separation channel V4, the first constant-quantity channel V5, the second constant-quantity channel V6, the first exhaust channel V7, the overflow channel V8, the second exhaust channel V9 and the third exhaust channel V10 are slots formed on the base surface b100 of the main board B1.

With respect to the function of the plurality of flow paths B1 of the main board B1 of the flow-path structure M1, each flow path b1 mainly comprises the injection unit G0, the uniform dividing unit G1, the separation unit G2, the exhaust unit G3, the overflowing unit G4 and the detection unit G5.

The injection unit G0 comprises the injection compartment F1 and the injection-hole cover pad F2, wherein the injection compartment F1 is connected to the plurality of flow paths B1, respectively.

The uniform dividing unit G1 comprises the uniform dividing compartment C1, the buffering compartment C2, the first channel V1, the second channel V2 and the third channel V3. In one embodiment, the uniform dividing compartment C1 is a circular slot formed on the base surface b100 of the main board B1 and utilized to constitute an accommodation space for the injection compartment F1. The uniform dividing compartment C1 has a droplet-like hollow structure (e.g., three-dimensional micro structure) formed with a slanted surface c100, or the uniform dividing compartment C1 has a droplet-like streamline profile from a top view thereof and is a micro structure provided with a chamfered slop at one side thereof. The uniform dividing compartment C1 has a section gradually reduced away from the reference position X0. Because the structure of the uniform dividing compartment C1 has a depth hi of an end nearby the injection compartment F1 greater than a depth ho of the other end away from the injection compartment F1, the flow resistance distribution of the uniform dividing compartment C1 is gradually increased. Further, with the smooth and streamline profile of the uniform dividing compartment C1, bubbles do not form in the uniform dividing compartment C1 during the injection process of the working fluid K. The buffering compartment C2 is a buffering slot disposed on the base surface b100 of the main board B1 and distributed along the radial direction X1 relative to the reference position X0 of the reference axis a1-a1. The design of the geometrical structure of the buffering compartment C2 is similar to that of the uniform dividing compartment C1. Because the structure of the buffering compartment C2 has a depth of an end nearby the uniform dividing compartment C1 greater than a depth of another end away from the uniform dividing compartment C1, the buffering compartment C2 has a curved variation of depth hs. The first channel V1 is a hollow portion disposed between the bottom of the injection compartment F1 and the bottom of the uniform dividing compartment C1 to connect the injection compartment F1 to the uniform dividing compartment C1. The second channel V2 is a linear capillary channel or slot disposed on the base surface b100 of the main board B1 and distributed along the radial direction X1 relative to the reference position X0 of the reference axis a1-a1. The third channel V3 is a linear capillary channel or slot disposed on the base surface b100 of the main board B1 and distributed along the radial direction X1 relative to the reference position X0 of the reference axis a1-a1 to connect the buffering compartment C2 to the collecting compartment C3. The second and third channels V2 and V3 serve as passive valves.

The separation unit G2 comprises the collecting compartment C3 and the separation channel V4. In this embodiment, the separation channel V4 is a capillary channel made by hydrophila molecule material (e.g., carboxylic acid (RCOOH), hydroxylation (ROH), amides group, ether group) containing a hydrophilic group. The collecting compartment C3 is a collecting slot disposed on the base surface b100 of the main board B1 and distributed along the radial direction X1 relative to the reference position X0 of the reference axis a1-a1, and one side of the collecting compartment C3 is connected to the third channel V3 of the uniform dividing unit G1, i.e., the third channel V3 is disposed between the buffering compartment C2 and the collecting compartment C3. The collecting compartment C3 comprises a first collecting region C32, a second collecting region C34 and a third collecting region C36. The first collecting region C32 connected to the third channel V3 serves as an upstream region of the collecting compartment C3, and the third collecting region C36 serves as a downstream region of the collecting compartment C3. The second collecting region C34 is located and connected between the first collecting region C32 and the third collecting region C36.

Figure 4A:
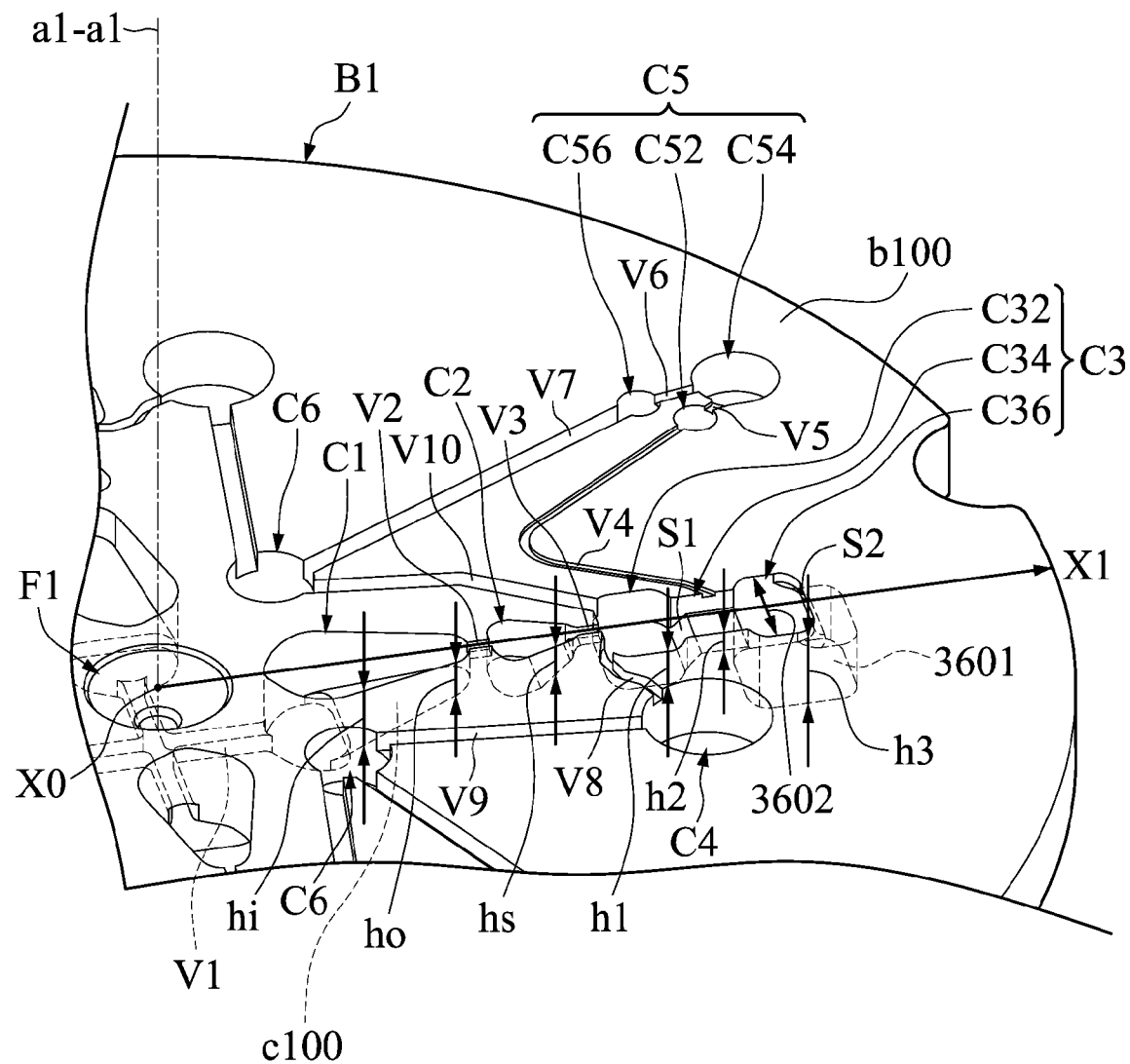
FIG. 4A is a partial perspective view of a single flow path of the flow-path structure from a zone (Y) of FIG. 3B.

FIG. 4A is a partial perspective view of a single flow path B1 of the flow-path structure M1 from a zone Y of FIG. 3B. The first collecting region C32, the second collecting region C34 and the third collecting region C36 of the collecting compartment C3 are slots formed with different depths from each other. A slanted surface S1 is disposed between the first collecting region C32 and the second collecting region C34 relative to the base surface b100. The third collecting region C36 of the collecting compartment C3 has a similar L-shaped sinking chamber 3601 formed with an opening 3602 which is connected to the second collecting region C34 and the base surface b100. The similar L-shaped sinking chamber 3601 further includes a C-shaped sidewall S2 adjacent to the opening 3602 and facing toward the second collecting region C34 and the third collecting region C36. A difference h1-h2 is formed between the depth h1 of the first collecting region C32 and the depth h2 of the second collecting region C34. Another difference h3-h2 is formed between the depth h3 of the third collecting region C36 and the depth h2 of the second collecting region C34.

Figure 4B:
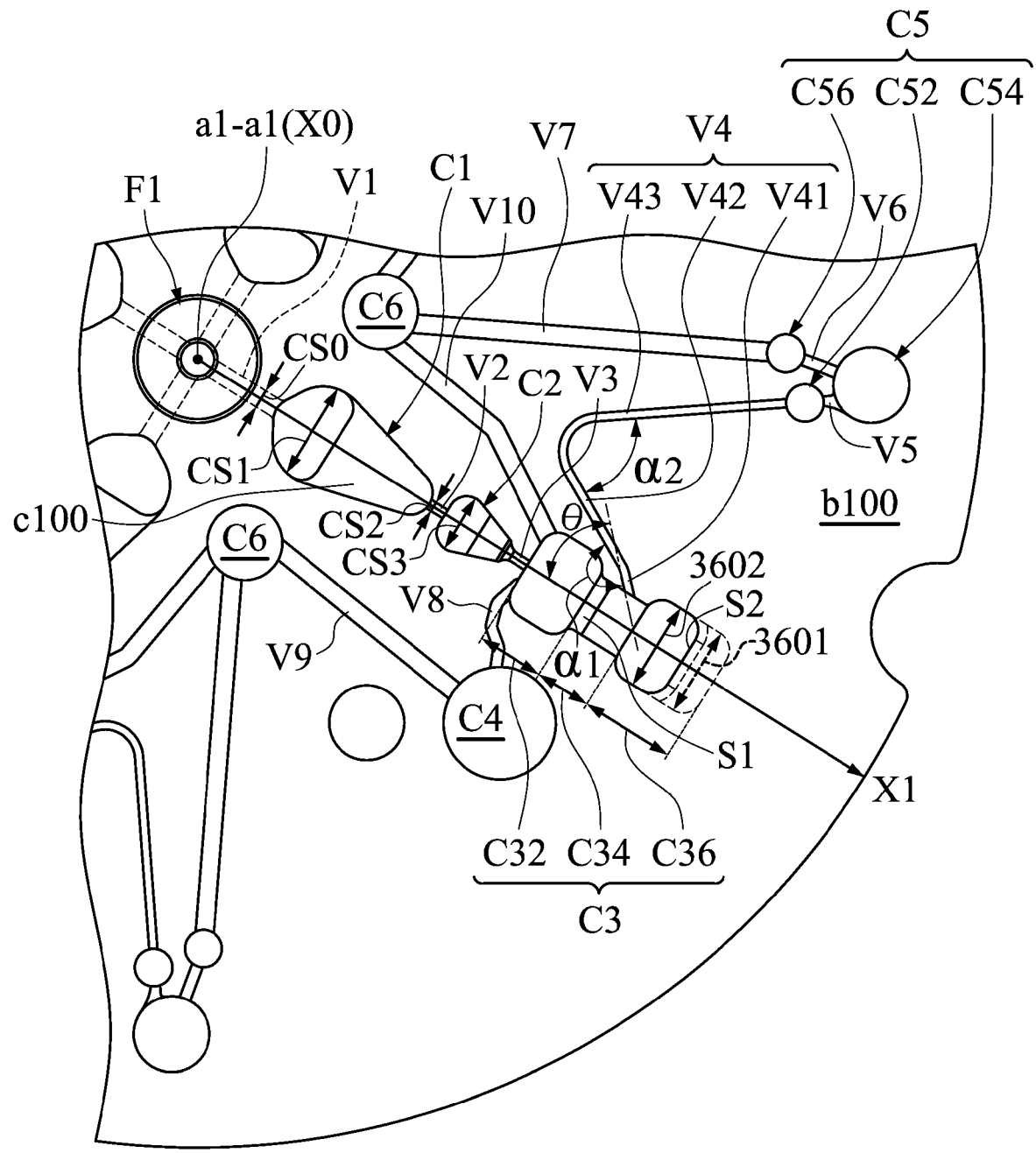
FIG. 4B is a partial top view of a single flow path of the flow-path structure in FIG. 3B.

Referring also to FIG. 4B, FIG. 4B is a partial top view of a single flow path b1 of the flow-path structure M1 in FIG. 3B. The separation channel V4 is a similar V-shaped linear capillary channel or a similar V-shaped slot disposed on the base surface b100 of the main board B1. That is, the separation channel V4 has hydrophila properties. The depth of the separation channel V4 is far less than the depth h1 of the first collecting region C32 of the collecting compartment C3, or the depth of the separation channel V4 is far less than the depth h2 of the second collecting region C34 or the depth h3 of the third collecting region C36 of the collecting compartment C3. As shown in FIG. 4B, the separation channel V4 is substantially formed by a first segment V41, a second segment V42 and a third segment V43. The first segment V41/the second segment V42 and the third segment V43 are formed into V-shape structure, wherein the first segment V41 is obliquely connected to the second collecting region C34 of the collecting compartment C3, the second segment V42 is connected between the first segment V41 and the third segment V43, the third segment V43 is connected to the detection compartment C5, and the second segment V42 is connected between the first segment V41 and the third segment V43. An oblique angle θ, formed between an extending direction of the first segment V41 of the separation channel V4 and an extending direction (i.e., the radial directions X1) of the second collecting region C34 of the collecting compartment C3, is preferably not greater than 30 degrees. In this embodiment, the oblique angle θ is 23 degrees. With respect to the first segment V41 of the separation channel V4, a first angle α1 formed between the first segment V41 and the second segment V42 is preferably not less than 90 degrees, and a second angle α2 formed between the second segment V42 and the third segment V43 is preferably not greater than 90 degrees. In this embodiment, the first angle α1 is 163 degrees, and the second angle α2 is 64 degrees. In particular, a rounded structure is provided between the second segment V42 and the third segment V43 of the separation channel V4.

In FIG. 3B, the exhaust unit G3 comprises the exhaust compartment C6, the first exhaust channel V7 and the second exhaust channel V9. The detection compartment C5 comprises a first constant-quantity region C52, a detecting region C54 and a second constant-quantity region C56. The exhaust compartment C6 is a cylindrical exhaust slot disposed on the base surface b100 and connected to the first, second and third exhaust channels V7, V9 and V10. The first, second and third exhaust channels V7, V9 and V10 are linear capillary channels or slots disposed on the base surface b100 of the main board B1, wherein the first exhaust channel V7 is connected to the second constant-quantity region C56 of the detection compartment C5, the second exhaust channel V9 is connected to the overflowing compartment C4, and the third exhaust channel V10 is connected to the first collecting region C32 of the collecting compartment C3. The depths of the first and second exhaust channels V7 and V9 is less than that of the second constant-quantity region C56 or the exhaust compartment C6. In this embodiment, the first constant-quantity region C52 and the detecting region C54 of the detection compartment C5 are recesses.

In FIG. 3B, the overflowing unit G4 comprises the overflowing compartment C4 and the overflow channel V8. The overflowing compartment C4 is a cylindrical exhaust slot disposed on the base surface b100 and connected to the overflow channel V8. The overflow channel V8 is a linear capillary channel or slot disposed on the base surface b100 of the main board B1. The depth of the overflow channel V8 is far less than that of the overflowing compartment C4.

Referring also to FIGS. 5A-5B and 7A-7B, the detection unit G5 comprises the detection compartment C5 and a plurality of objects Q with a first marked substance. The objects Q are selectively disposed in the uniform dividing compartment C1 and/or the buffering compartment C2. The first constant-quantity region C52 of the detection compartment C5 is connected to the detecting region C54 through the first constant-quantity channel V5, and the second constant-quantity region C56 is connected to the connected to the detecting region C54 through the second constant-quantity channel V6. In this embodiment, the detecting region C54 of the detection compartment C5 is a cylindrical detecting slot, the objects Q are glass balls or glass micro-balls with a diameter ranged from 10 nanometers (nm) to 1,000 micrometers (μm), and the first marked substance of the objects Q are a conjunctive DNA or RNA, a protein, a biomarker, an antibody, a cell, or other biomolecular. Additionally, it is noted that the glass balls are formed by a pre-treatment process (e.g., physical or chemical method) with a single step or multiple steps, so that the function of catching particular targets can be achieved. A covering thin film is formed on the surfaces of the glass balls by a physical method (e.g., heated under a high temperature, absorbed or deposited) or chemical method (e.g., using amination (—HH2), hydrogenation (—OH), a carboxyl group (—COOH) or an aldehyde group (—CHO), etc.). Additionally, in other embodiments, the detection unit can be included into the separation unit, and the objects can be magnetic balls, physical carriers or other structs.

Therefore, biochemical reaction or optical detection can be performed by the constant-quantity collection of the first component, excess separated components can be prevented from flowing into the detection compartment, product detection yield can be increased, and different assay detections can be carried out with a small sample volume at the same time.

FIGS. 5A to 5E are schematic views showing the operation of the analytical system I. In FIGS. 5A-5E, the working fluid K is blood, the first component k01 is plasma, and the second component k02 is blood cell or haemocyte having specific gravity greater than that of blood.

Figure 5A:
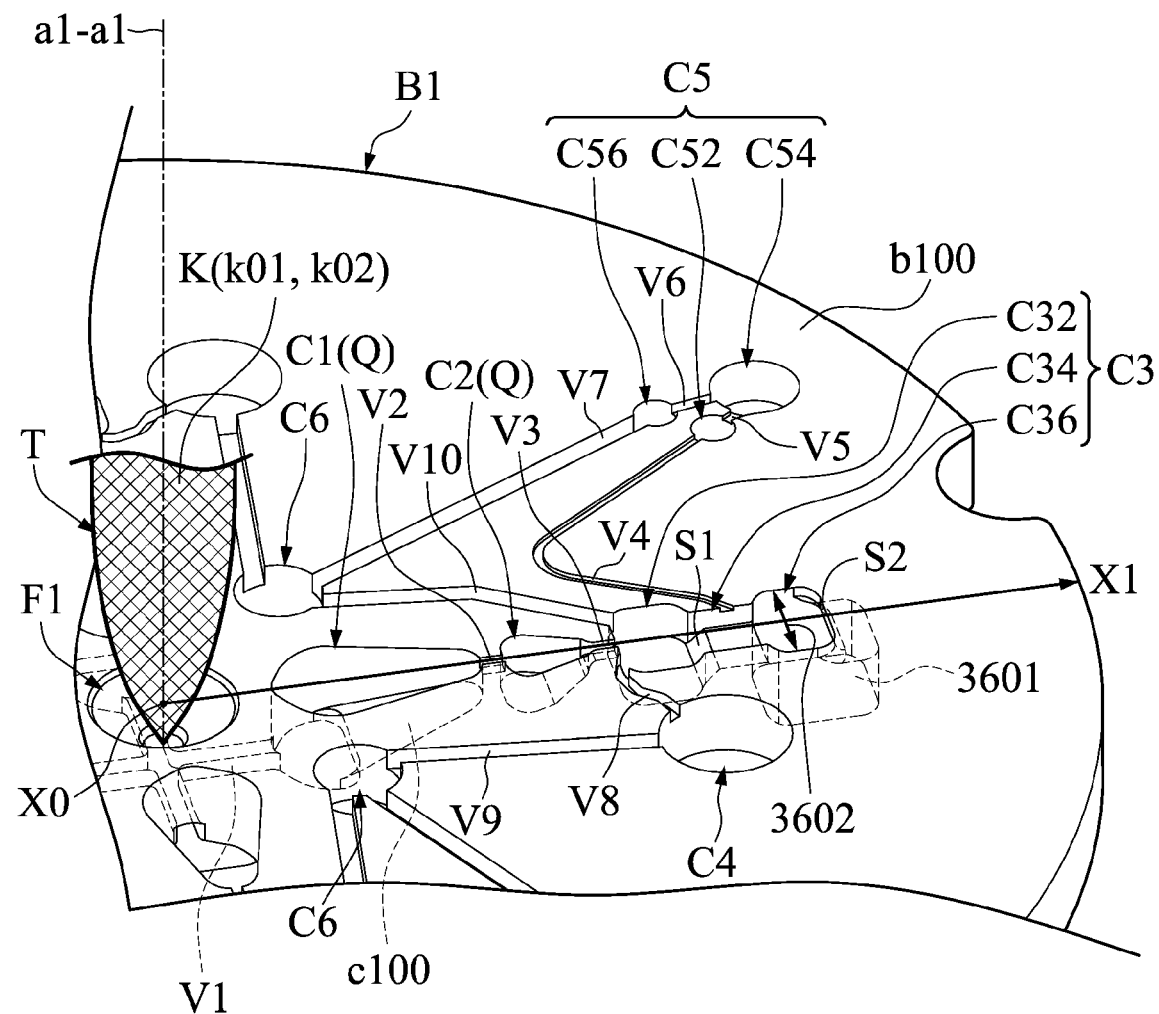
FIG. 5A is a schematic view of a working fluid injected to a uniform dividing compartment and a buffering compartment of the single flow path.
Figure 5B:
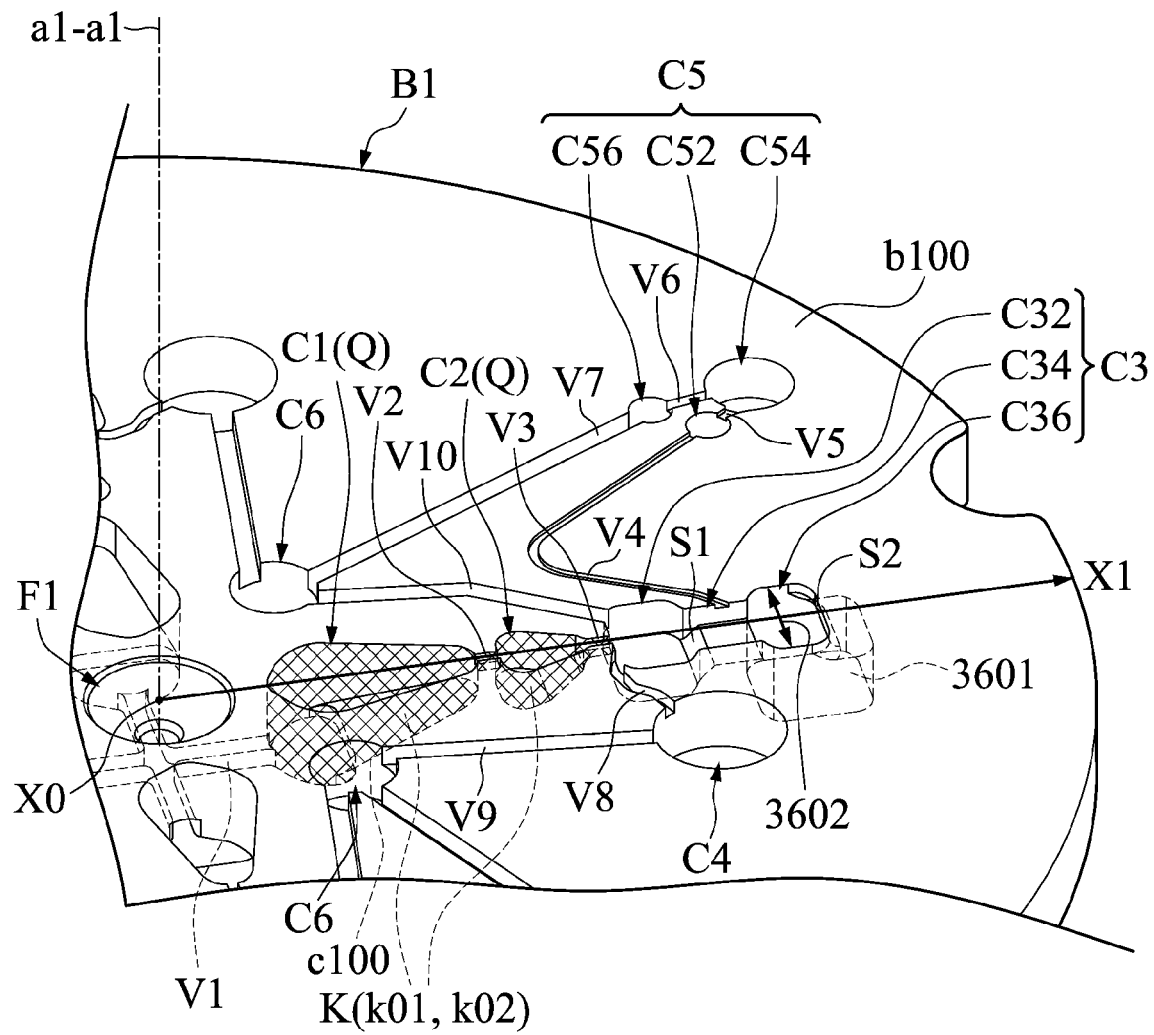
FIG. 5B is a schematic view of a partial flow field of the working fluid located in the uniform dividing compartment and the buffering compartment of FIG. 5A after a uniform division process.

FIG. 5A is a schematic view of the working fluid K with a predetermined volume (e.g., 60 μL) transmitted to the injection compartment F1 of the flow-path structure M1, and FIG. 5B is a schematic view of the working fluid K located in the uniform dividing compartment C1 and the buffering compartment C2 of FIG. 5A after a uniform division process. In FIGS. 5A and 5B, the plurality of objects Q are selectively disposed in the uniform dividing compartment C1 and/or the buffering compartment C2, so that the working fluid K can be detected by the plurality of objects Q.

Due to the droplet-like/three-dimensional geometrical structure of the uniform dividing compartment C1 and the buffering compartment C2 and capillary structure of the third channel V3, the working fluid K is merely filled in the first channel V1, the uniform dividing compartment C1, the buffering compartment C2, the second channel V2 and the third channel V3 of the uniform dividing unit G1 (i.e., the working fluid K is uniformly distributed to each of the uniform dividing compartment each of C1 and each of the buffering compartments C2) when the working fluid K is injected into the uniform dividing compartment C1 and the buffering compartment C2 through the injection compartment F1. That is, when the working fluid K is injected into the uniform dividing compartment C1 and the buffering compartment C2 from the injection compartment F1, the working fluid K does not enter the collecting compartment C3 of the separation unit G2 and an injection error of the working fluid K can be adjusted and controlled by the buffering compartment C2.

In other embodiments, a capillary tube (not shown in FIGs.) can be utilized to directly access the working fluid K, except the described pipette utilized to access the constant-quantity working fluid K prior to the injection process. Then, the capillary tube fully accessing the working fluid K can be inserted into the center of a sampler to automatically distribute the working fluid to each of the uniform dividing slots by hydrophila membranes.

The working fluid K comprises a second marked substance which can be a markable complementary DNA or RNA, a substrate, an enzyme, a coenzyme, a complement, an antigen, other cells or biomolecular. When the working fluid K and the objects Q located in the uniform dividing compartment C1 and the buffering compartment C2 are motionlessly placed and reacted for a predetermined time period, the second marked substance of the working fluid K bonds to the first marked substance of the objects Q by the connection of targets, thus, forming bio composites BIO-CO (see FIG. 7B).

Figure 5C:
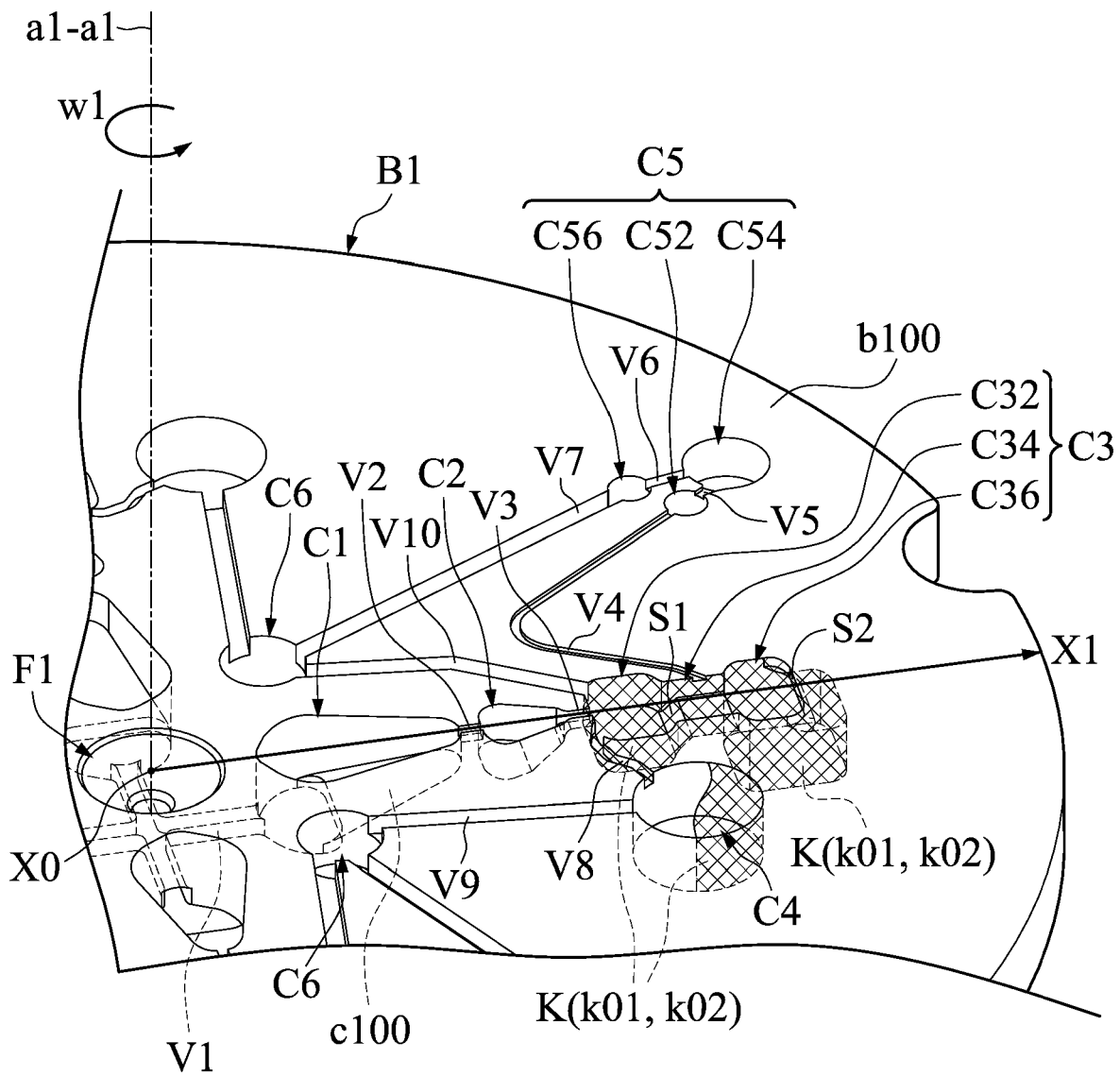
FIG. 5C is a schematic view showing the working fluid being distributed to a collecting compartment and an overflowing compartment after the main board is rotated about a first direction relative to a reference position (X0) of a reference axis (a1-a1)

FIG. 5C is a schematic view showing the status of the main board B1 after the main board B1 is rotated about a first direction w1 relative to the reference position X0 of the reference axis a1-a1.

When the main board B1 is rotated about a first direction w1 relative to the reference position X0 of the reference axis a1-a1, the working fluid K located in the uniform dividing compartment C1 and the buffering compartment C2 is transmitted to the first collecting region C32, the second collecting region C34 and the third collecting region C36 of the collecting compartment C3 at a first predetermined time period, and the separation of the first and second components k01 and k02 of the working fluid K located in the first collecting region C32, the second collecting region C34 and the third collecting region C36 of the collecting compartment C3 is performed at a second predetermined time period, wherein the first predetermined time period is prior to the second predetermined time period, and the first collecting region C32 and the second collecting region C34 of the collecting compartment C3 are filled with the separated first component k01. In this embodiment, the first direction w1 is a counter clockwise (CCW) direction, the rotation speed is designed as 4,000 RPM, the rotation of the first predetermined time period includes a first step (pre-step) for performing an accelerated motion (run time: 0 to 5 second, speed: 0-4,000 rpm), and the second predetermined time period includes a second step (post-step) for performing a uniform velocity motion (run time: 5 to 60 sec, speed: 4,000 rpm).

When the accelerated motion of the first step is performed (run time/the first predetermined time period: 0 to 5 sec, speed: from 0 to 4,000 rpm), a centrifugal force under a high rotation speed drives the working fluid K located in the uniform dividing compartment C1 and the buffering compartment C2 to flow through the third channel V3 to the first collecting region C32, the second collecting region C34 and the third collecting region C36 of the collecting compartment C3 and the overflowing compartment C4.

Due to the second component k02 having a specific gravity greater than that of the first component k01, under the opening 3602, and the C-shaped sidewall S2 of the third collecting region C36 of the collecting compartment C3, when the uniform velocity motion of the second step is performed (run time/the second predetermined time period: from 5 to 60 sec, speed: 4,000 rpm), the second component k02 having a specific gravity greater than that of the first component k01 is kept at the lower side of the third collecting region C36 of the collecting compartment C3 under the rotational centrifugal force. Also, the separated first component k01 is kept at the upper side of the first collecting region C32, the second collecting region C34 and the third collecting region C36 of the collecting compartment C3, and the separated first component k01 is also kept at the separation channel V4 by the rotational centrifugal force.

Figure 5D:
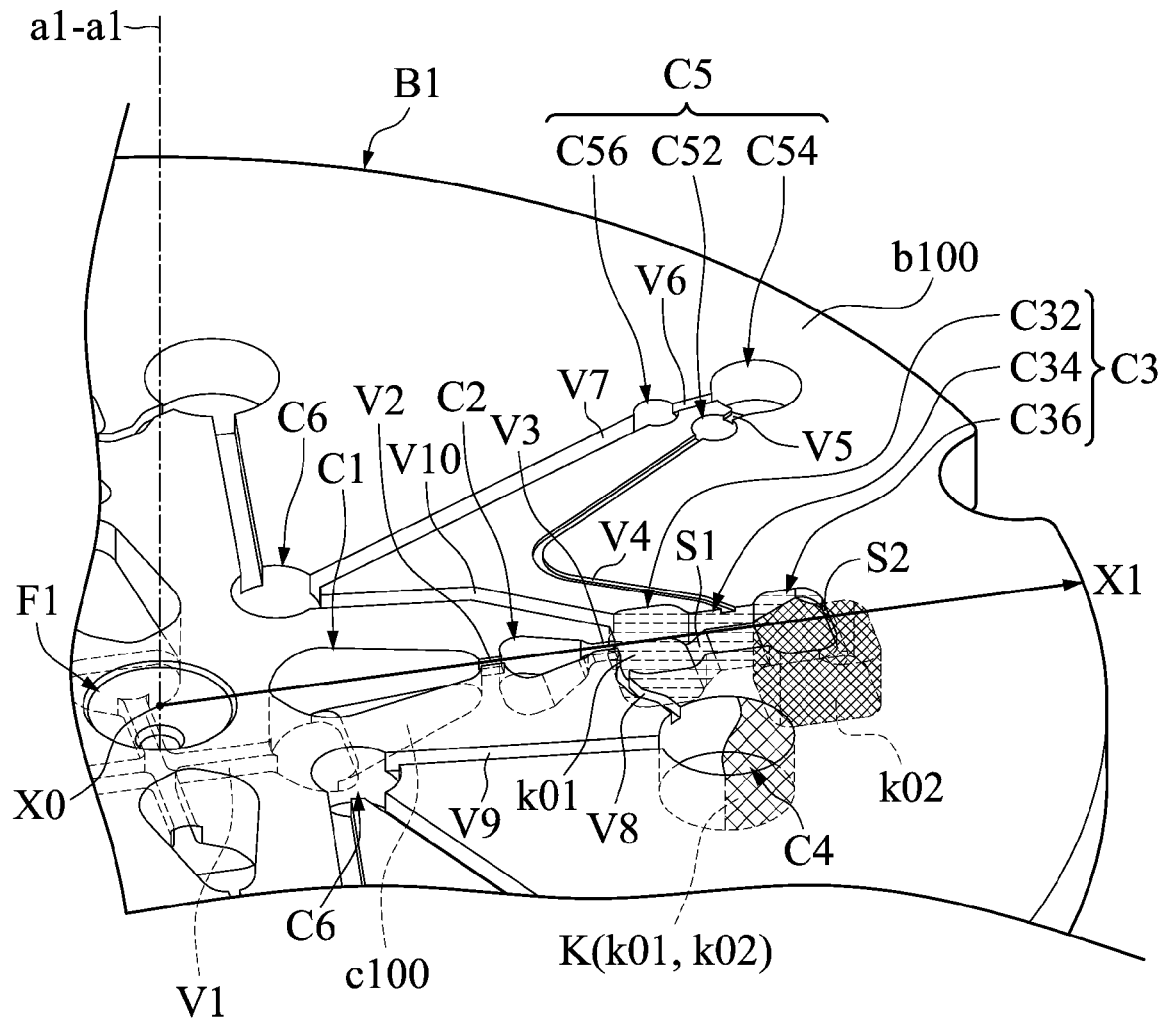
FIG. 5D is a schematic view showing the separated first component and the separated second component being distributed to the collecting compartment after the rotating main board is stopped.

FIG. 5D is a schematic view of the separated first component k01 being transmitted to the separation channel V4 when the main board B1 of FIG. 5C is stopped and delayed after a particular time period. Because of the capillary function formed on the first collecting region C32 and the second collecting region C34 of the collecting compartment C3 and the separation channel V4, the separated first component k01 is transmitted to the detection compartment C5 through the separation channel V4 when the main board B1 is stopped and delayed for a particular time period.

Figure 5E:
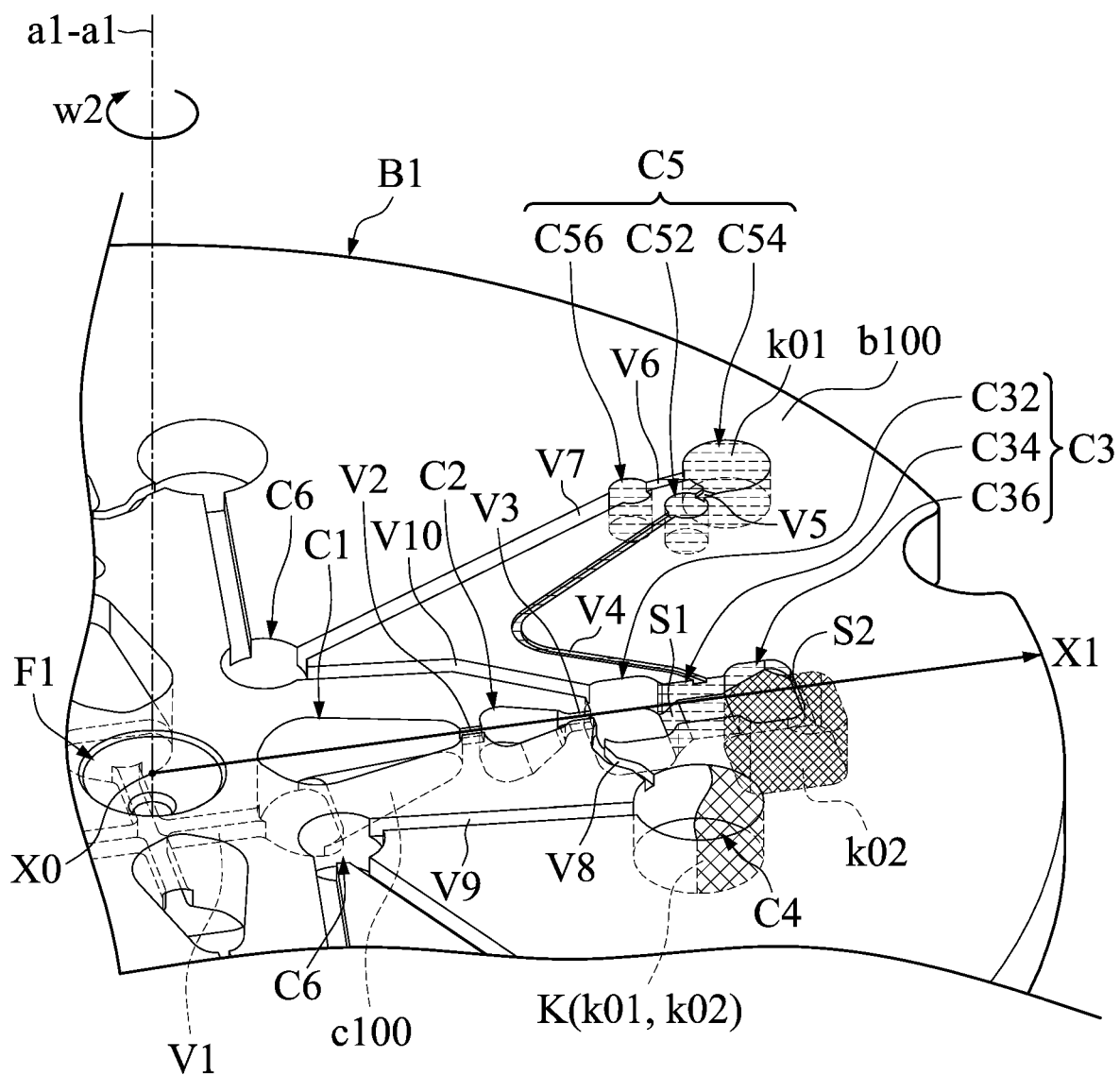
FIG. 5E is a schematic view showing the separated first component being fully transmitted to a constant-quantity detection compartment after the main board that was stopped, which is shown in FIG. 5D, begins to rotate again about the first direction or a second direction relative to the reference position (X0) of the reference axis (a1-a1)

FIG. 5E is a schematic view of the main board B1 of the flow-path structure M1 that was stopped, which is shown in FIG. 5D, beginning to rotate again about the first direction w1 or a second direction w2 at a low velocity relative to the reference position X0 of the reference axis a1-a1. In this embodiment, the second direction w2 is a clockwise (CW) direction.

When the main board B1 that was stopped begins to rotate again about the first direction w1 or the second direction w2 at a low velocity (speed: 2,000 to 2,500 RPM, run time: 5 to 15 sec), the separated first component k01 located in the first collecting region C32 and the second collecting region C34 of the collecting compartment C3 is outwardly transmitted through the separation channel V4 under an acting force which is the resultant force of the Coriolis force and the siphon force. Thus, the first component k01 is completely separated from the second component k02 and fills the first constant-quantity region C52, the detecting region C54 and the second constant-quantity region C56 of the detection unit G5. In the capillary filling process, the first constant-quantity region C52 and the second constant-quantity region C56 of the detection unit G5 serve as constant-quantity valves for the entering working fluid K. With respect to all of the first constant-quantity regions C52, the detecting regions C54 and the second constant-quantity regions C56 of the detection units G5, after one of the first constant-quantity regions C52 is fully filled by the separated first component k01, the remaining unfilled first constant-quantity regions C52 are sequentially fully filled by the separated first component k01. Then, the separated first component k01 enters the first constant-quantity channel V5 to fill up one of the detecting regions C54, and then the remaining detecting regions C54 are sequentially fully filled by the separated first component k01. Finally, the separated first component k01 enters the second constant-quantity channel V6 to fill up one of the second constant-quantity regions C56, and then the remaining second constant-quantity regions C56 are sequentially fully filled by the separated first component k01. In the described filling processes, over, under, or non-uniformed filling for all detecting regions C54 are mitigated. Therefore, the constant-quantity first component k01 can be accurately transmitted to each of the detecting regions C54. Further, the separated first component k01 can be reacted with a reaction reagent (not shown in FIGs.) preset in the detecting region C54.

In another embodiment (not shown in FIGs.) where the reaction reagent is not preset in the detecting region C54, when the first component k01 is completely separated from the second component k02 and filled in the detecting region C54 of the detection compartment C5 of the detection unit G5, it is possible to check whether the color of the first component k01 located in the detecting region C54 is transparent yellow or not and whether the tested blood (e.g., the working fluid K) is hemolytic or not. If the color of the first component k01 located in the detecting region C54 is red, it is determined that the tested blood specimen has failed the test, i.e., the tested blood is hemolytic and not suitable to be a specimen for cartridge testing, and the described sampling process must be repeated.

According to the location of all chamber and compartment structures, it is known that the location of the detecting region C54 of the detection compartment C5 of the detection unit G5 has a maximum rotation radius relative to the reference position X0 of the reference axis a1-a1, thereby increasing the stability of the reagent located in the detecting region C54 of the detection compartment C5 of the detection unit G5. In the described steps of the analytical method, the division process and the separation process can be normally operated when gases from all slotted structures are expelled by the exhaust compartment C6, and the first, second and third exhaust channel V7, V9 and V10 of the exhaust unit G3. Further, the division/separation processes and the exhaust process of the uniform dividing unit G1 and the separation unit G2 are simultaneously operated and the overflowing unit G4 collects the excess injected working fluid, so that the division/separation processes thereof can be normally operated.

Figure 6A:
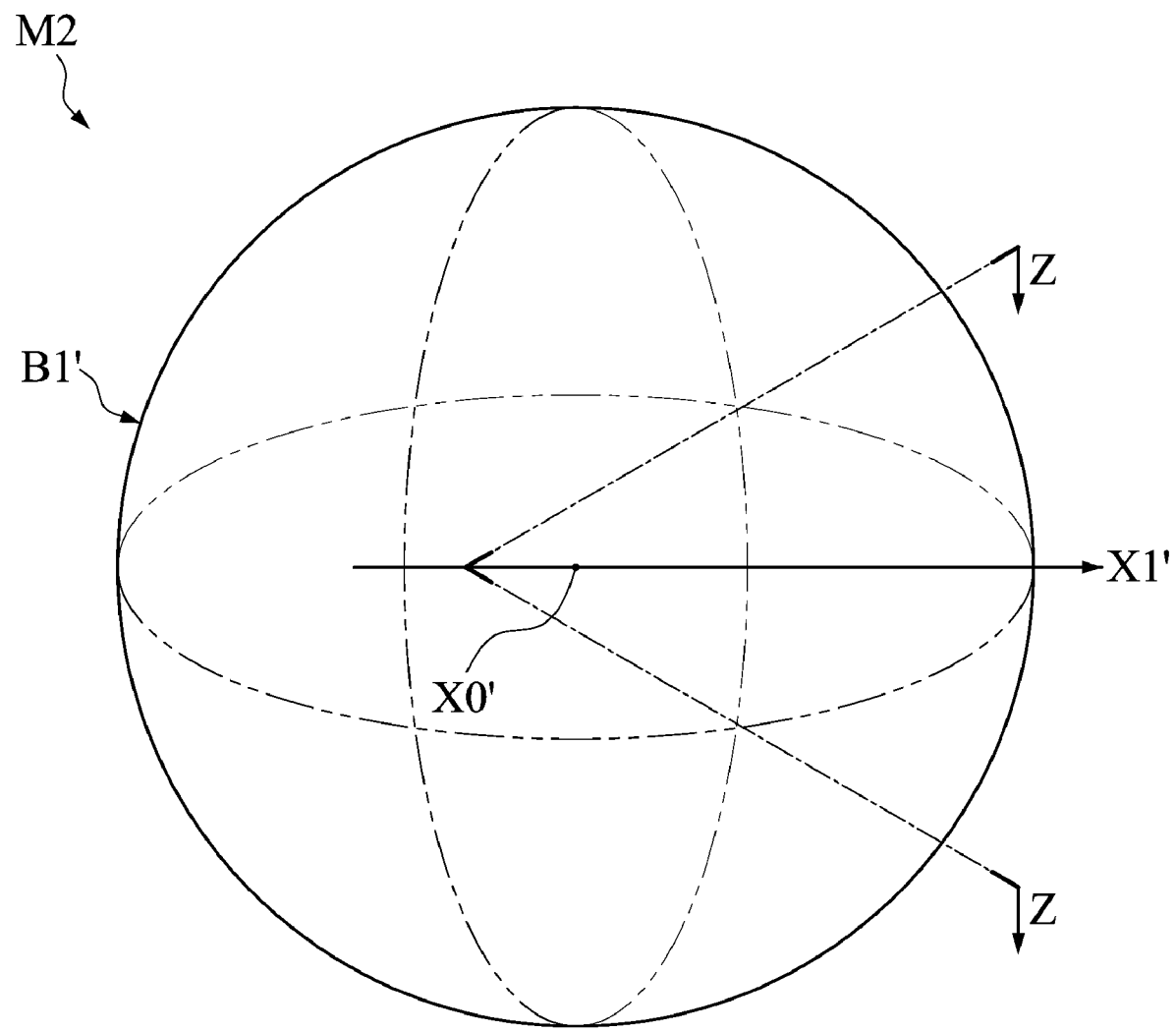
FIG. 6A is a perspective view of a flow-path structure of a second embodiment of the invention.
Figure 6B:
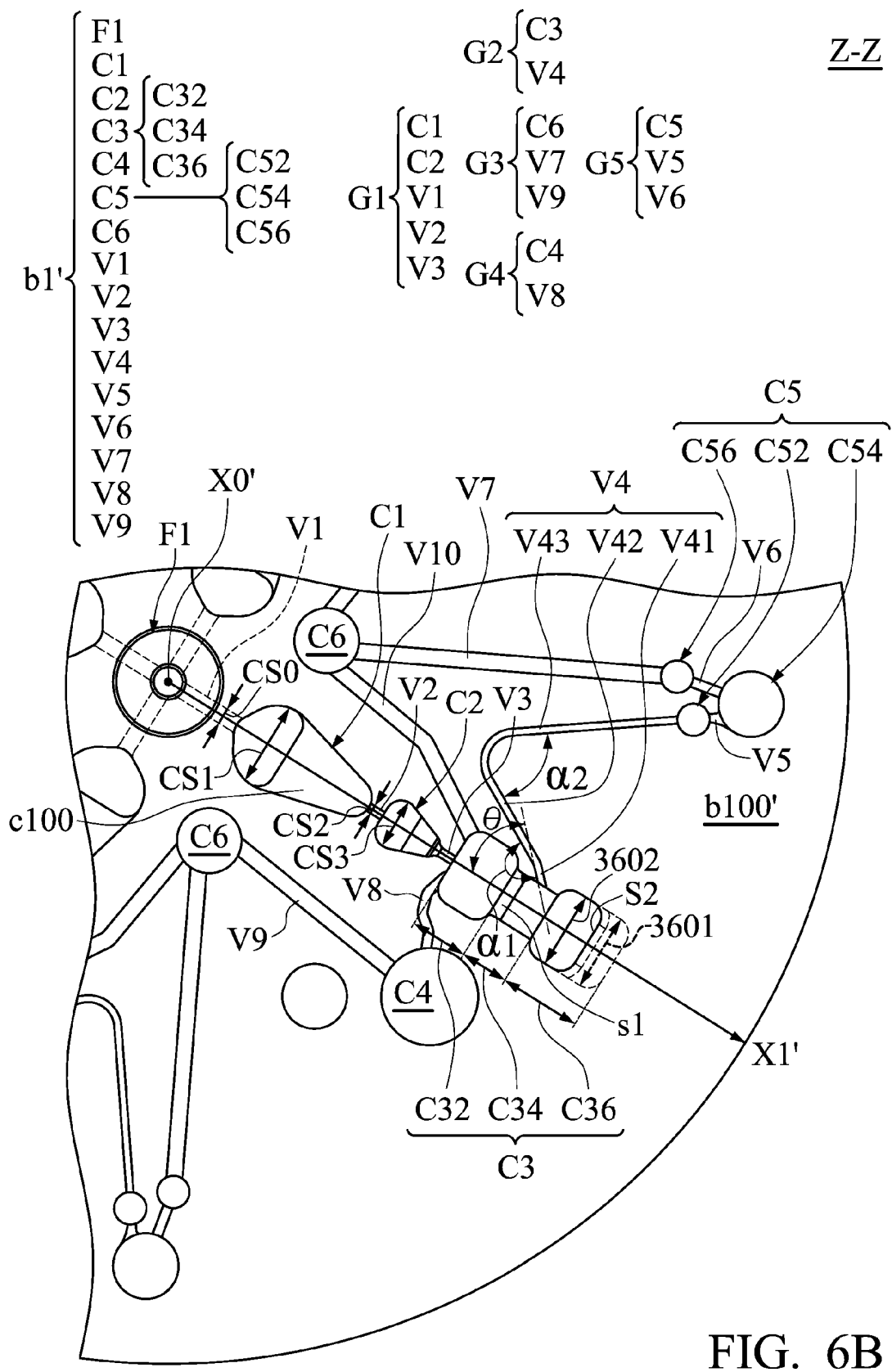
FIG. 6B is a sectional view taken along a line (Z-Z) of the flow-path structure of FIG. 6A.

FIG. 6A is a perspective view of a flow-path structure M2 of a second embodiment, and FIG. 6B is a sectional view taken along a line Z-Z of the flow-path structure M2 relative to a radial direction X1' of FIG. 6A.

In FIG. 6A, the flow-path structure M2 comprises a spherical main body B with a reference position X0' (e.g., center of sphere). From the sectional view taken along the line Z-Z of the flow-path structure M2 relative to the radial direction X1' of FIG. 6A, one flow path b1' of the flow-path structure M2 can be obtained as shown in FIG. 6B. The spherical main body B1' comprises a base surface b100' and a plurality of flow paths b1' which are formed on the base surface b100' and rotated about the reference position X0'. In this embodiment, the geometrical structure and configuration of the flow paths b1' of the flow-path structure M2 are substantially the same as that of the flow paths B1 of the flow-path structure M1 of the first embodiment, and thus the same structures and configurations are omitted hereafter.

The related applications of the analytical system I and the flow-path structure M1 thereof are described below.

In FIG. 5B, when the working fluid K (blood) located in the uniform dividing compartment C1 and the buffering compartment C2 of the flow-path structure M1 are motionlessly placed and reacted for the predetermined time period, the objects Q (glass micro-balls) located in the uniform dividing compartment C1 and the buffering compartment C2, the tested targets and the markable biomolecular (second marked substance) are bonded. In a fluorescent detection process, the first biomolecular are capable of bonding with the second biomolecular having chromophore by the tested target molecular, and a fluorescent signal can be read from the detecting region C54 of the detection compartment C5. In a cold-light or light-absorbed detection process, after the first biomolecular bonds to the second biomolecular via the target to be tested, the bonded first and second biomolecular located in the detecting region C54 of the detection compartment C5 can react with the added substrates SUB. Thus, a cold-light or light-absorbed optical signal or luminous product L can be obtained.

By bonding the first biomolecular to the second biomolecular via the target to be tested, the bio composite BIO-CO is formed (see FIG. 7B), and the other non targets (non-TA) to be tested (see FIGS. 7A and 7B) having no reaction thereof is suspended in the working fluid. When the flow-path structure M1 disposed on a systematic rotating table (not shown in FIGs.) is rotated at a high speed about the injection compartment F1 thereof, the working fluid K (blood) passes through the third channel V3 (check valve), and the first component k01 (plasma) and the second component k02 (blood cell) are centrifugally separated into different layers due to different specific gravities. Thus, the second component k02 (blood cell) is accumulated at the lower side of the collecting compartment C3 and the first component k01 (plasma) is accumulated at the upper side of the collecting compartment C3.

Because the volume of the object Q (glass micro-ball) bonded to the tested target is greater than the pore size of the third channel V3, the objects Q (glass micro-balls) are blocked and kept in the collecting compartment C3, and the other non-bonded luminous dyes accompanied with the first component k01 (plasma) flow to the lower side of the collecting compartment C3. Due to the capillary force of the miniature flow path, the first component k01 (plasma) sequentially passes through the separation channel V4 and flows to the detection compartment C5.

Figure 7A:
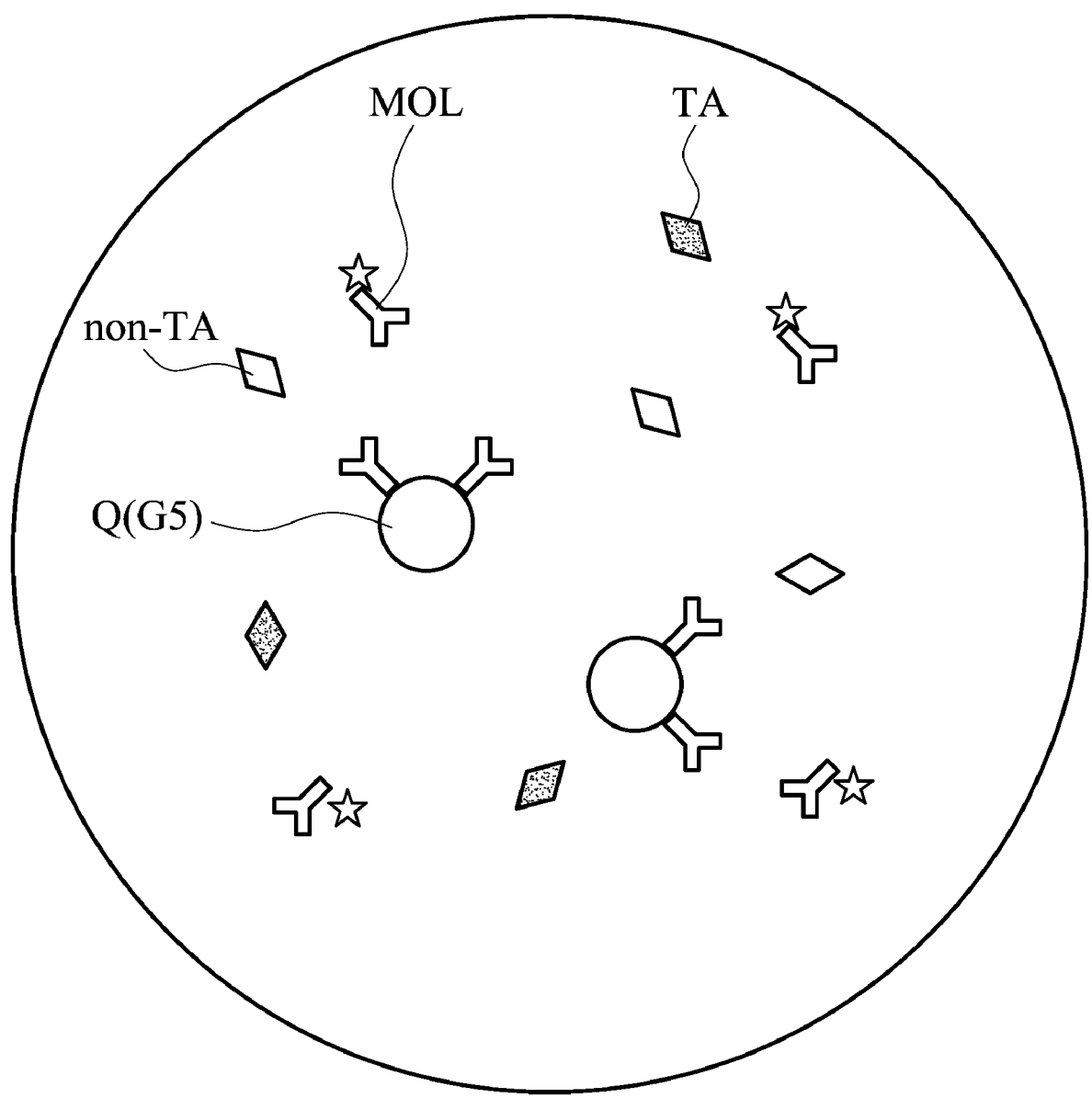
FIGS. 7A to 7C are schematic views of biochemical reaction and optical detection performed by an analytical system of the invention.
Figure 7B:
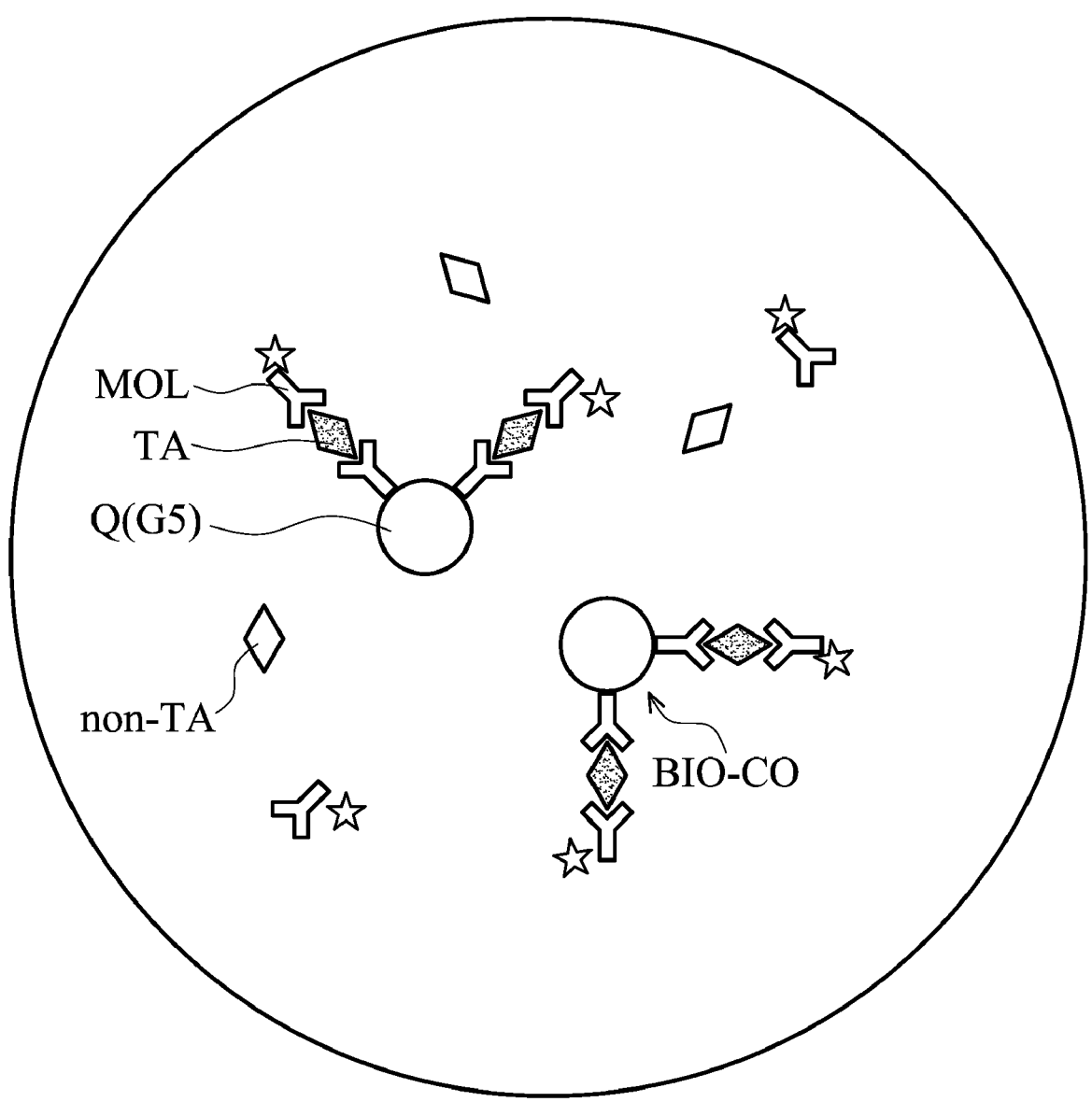
Figure 7C:
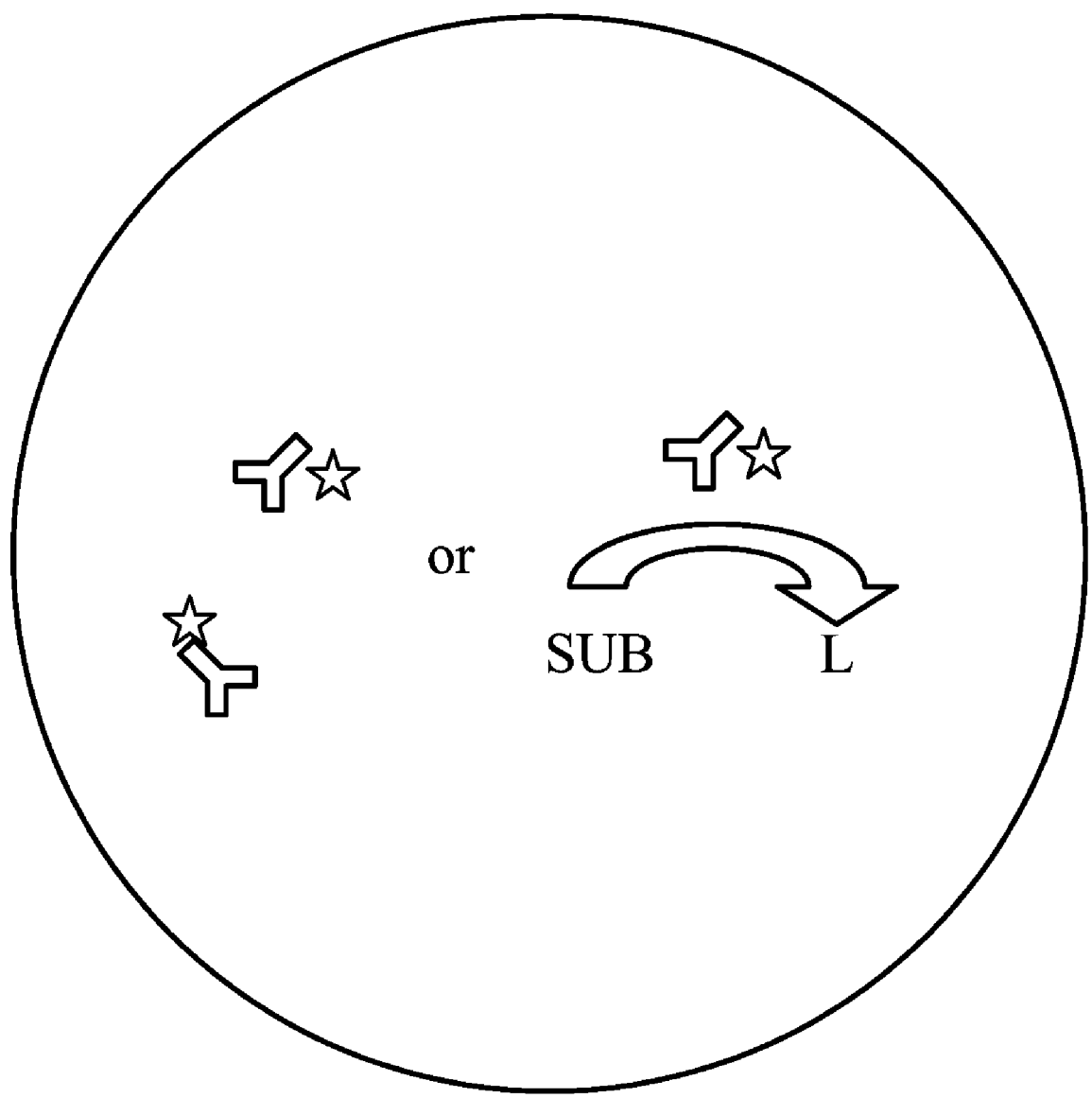

FIGS. 7A, 7B and 7C are schematic views of biochemical reaction and optical detection performed by the analytical system I of the embodiment.

In FIG. 7A, the objects Q (glass micro-balls) and the target molecules MOL are added in the uniform dividing compartment C1 and the buffering compartment C2, and the fluorescent signal within the detection compartment C5 can be read from an upper or a lower side of the uniform dividing compartment C1 and the buffering compartment C2 by an optical detection system. When a particular target molecule of the working fluid K appears (see FIG. 7B), the surface-treated object Q (glass micro-ball) bonds to the particular target, and then the second reactant carried with the target molecules MOL bonds to the connected object Q and the particular target. Thus, a bio composite is formed on the object Q (glass micro-ball). In FIG. 7C, the other non-bonded biomolecular and the target molecules MOL driven by the centrifugal force enter a detection zone. The quantity and concentration of the target molecules MOL can be determined by an optical system located in the detection compartment C5 according to luminous intensity, and the quantity of the target molecules actually reacting with the object Q (glass micro-ball) can be inferred according to the luminous intensity with a known total quantity.

The flow rate of the working fluid traveling in the flow-path structure of the described embodiments can be calculated by the following Formula 1.

$$Q = \frac{WH^3 \Delta P}{12\mu \Delta X} \qquad \text{Formula 1}$$

In Formula 1, Q represents a flow rate of the working fluid, W represents the width of the channels or slots, H represents depths of the channels or slots, $\Delta P$ represents pressure difference located at different sites, $\mu$ represents viscosity coefficient, and $\Delta X$ represents a traveling distance of the working fluid.

The flow resistance of the working fluid traveling in the flow-path structure with respect to the dimensions of the geometrical structure of flow-path structure of the described embodiments can be calculated by Formula (2).

$$R \propto \frac{1}{H^3} \qquad \text{Formula (2)}$$

In Formula (2), R represents a flow resistance of the working fluid.

Because the width and depth of the channels or slots are reduced gradually as the working fluid enters the uniform dividing compartment C1 through the injection compartment F1, if the flow rate is constant, the pressure difference required for the flow of the fluid is increased. In the injection process of the working fluid, when one uniform dividing compartment receives more volume of the working fluid than the other uniform dividing compartments, the increased flow resistance of the working fluid located at an exit thereof forces the working fluid to fill into the uniform dividing compartment(s) having lesser flow resistance, so that the uniform division and transmission of the working fluid can be simultaneously completed. With respect to high-viscosity working fluids (e.g., blood viscosity is about three to four times that of water, plasma viscosity is about one to two times that of the water), uniform division can be smoothly performed by the micro structure of the embodiments.

Referring to FIGS. 4B and 6B simultaneously, because the desired pressure of the working fluid can be precisely controlled by the locations and dimensions of the geometrical structure of the flow path of the embodiment, uniform division of the working fluids can be smoothly performed. Table 1 shows the values of pressure differences (unit: Pa) of the working fluid and structural dimensions (e.g., width and height) which were measured at different locations (e.g., locations CS0, CS1, CS2 and CS3, shown in FIG. 4B). In Table 1, the injection flow rate is set as 10 mm³/s, the traveling distance is set as 7.5 mm, and the viscosity of the working fluid is set as 3.2 mPa-s. It is understood that the smaller the structural dimensions are, the more pressure difference required for forcing the working fluid, and thus a baffle vale' effect can be provided. On the contrary, the larger the structural dimensions are, the less pressure difference required for forcing the working fluid. Thus, the working fluid can be uniformly divided at each of the uniform dividing compartments.

Table 1 shows the relation of pressure differences and structural dimensions measured at different locations.

TABLE 1

| Locations | Width (mm) | Height (mm) | Pressure difference of working fluid (Pa) |
|---|---|---|---|
| CS0 | 0.5 | 0.45 | 63.2 |
| CS1 | 2.67 | 2 | 0.134 |
| CS2 | 0.28 | 0.28 | 468 |
| CS3 | 1.62 | 1.5 | 0.197 |

Due to the baffle pressure difference of the fluid structure being lesser than the centrifugal force, the working fluid is uniformly filled in each of the collecting compartments when the working fluid injected into the uniform dividing compartments is rotated by a motor (not shown in FIGs.).

The described centrifugal force of the traveling working fluid can be calculated by the following Formula (3). In Formula (3), $P_{cent}$ represents centrifugal force, $\rho$ represents the density of the working fluid, f represents rotation speed, $r_1$ represents a rotation radius of an exit, and $r_0$ represents a rotation radius of an inlet.

$$P_{cent}=2\pi^2\rho f^2[r_1^2-r_0^2]$$ Formula (3)

Table 2 shows the calculation result of the centrifugal force of examples A to E under different rotation speeds when the blood density is 1060 kg/m³, the rotation radius $r_1$ of the exit is 7.5 mm, and the rotation radius $r_1$ of the exit is 2.5 mm.

Table 2 shows the relationship of rotation speed and centrifugal force of examples A to E.

TABLE 2

| Example | Rotation speed f (rpm) | Centrifugal force $P_{cent}$ (Pa) |
|---|---|---|
| A | 4000 | 4649 |
| B | 2000 | 1162 |
| C | 1269 | 468 |
| D | 1000 | 290 |
| E | 500 | 72 |

By incorporating formulas (1) and (3), the relationship of the variation of the structural dimension and the pressure difference of the flow resistance can be obtained, so that a desired centrifugal rotation speed can be determined to generate enough centrifugal force to overcome the resistance of a pass or an opening of the channels of the flow-path structure. The flow-path structure is rotated at the lower rotation speed to execute a uniform division process, wherein excess working fluid is transmitted to the overflowing compartment. Then, the flow-path structure is rotated at the higher rotation speed to execute a separation process of the working fluid.

During the uniform division and separation process, bubbles hindering the movement of the working fluid in the microchannel of the flow-path structure should be eliminated. With similar droplet-like uniform dividing compartments, bubbles can be averagely expelled out when the working fluid is injected into the compartments and channels. Further, bubbles are eliminated from the working fluid when the working fluid is injected, so that a smooth injection process for the injected working fluid among the uniform dividing compartments can be obtained, wherein the uniform-divided working fluid can be successfully transmitted to the collecting compartments.

While the invention has been described by way of example and in terms of the several embodiments, it is to be understood that the invention is not limited to the disclosed embodiments. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A flow-path structure for performing centrifugal separation of a working fluid comprising at least one first component and at least one second component with different characteristics therebetween, comprising:
    an injection compartment utilized for receiving the working fluid to be injected;
    an uniform dividing compartment connected to the injection compartment relative to a reference position to divide the working fluid transmitted from the injection compartment, comprising a section gradually reduced away from the reference position;
    a collecting compartment connected to the uniform dividing compartment, comprising a plurality of collecting regions connected to each other;
    a detection compartment; and
    a separation channel utilized to connect one of the plurality of collecting regions to the detection compartment;
    when the uniform dividing compartment is rotated relative to the reference position, the working fluid located in the uniform dividing compartment is transmitted to the plurality of collecting regions of the collecting compartment, and the at least one first component and the at least one second component of the working fluid are centrifugally separated from each other by the plurality of collecting regions of the collecting compartment; and
    when the rotating uniform dividing compartment is stopped relative to the reference position, the at least one first component of the working fluid located at the plurality of collecting regions of the collecting compartment is transmitted to the separation channel, and when the uniform dividing compartment that was stopped begins to rotate relative to the reference position, the at least one first component of the working fluid located at the separation channel is centrifugally transmitted to the detection compartment through the separation channel, so that the at least one first component is completely separated from the at least one second component.

2. The flow-path structure as claimed in claim 1, wherein the uniform dividing compartment comprises a droplet-like hollow structure formed with at least one slanted surface.

3. The flow-path structure as claimed in claim 1 further comprising a buffering compartment connected between the uniform dividing compartment and the collecting compartment relative to the reference position, comprising a section gradually reduced away from the reference position.

4. The flow-path structure as claimed in claim 3, wherein the buffering compartment comprises a droplet-like hollow structure.

5. The flow-path structure as claimed in claim 3, wherein the uniform dividing compartment, the buffering compartment and the collecting compartment are arranged along a radial direction passing through the reference position.

6. The flow-path structure as claimed in claim 1 further comprising an overflowing compartment connected to the collecting compartment, wherein when the overflowing compartment is rotated relative to the reference position, excess working fluid injected to the collecting compartment is transmitted to the overflowing compartment.

7. The flow-path structure as claimed in claim 1, wherein the detection compartment comprises a detecting region and a first constant-quantity region connected between the separation channel and the detecting region, wherein when the rotating uniform dividing compartment is stopped relative to the reference position, the at least one first component of the working fluid located at the plurality of collecting regions of the collecting compartment is transmitted to the separation channel, and when the uniform dividing compartment that was stopped begins to rotate relative to the reference position, the at least one first component of the working fluid located at the separation channel is centrifugally transmitted to the detecting region of the detection compartment through the separation channel and the first constant-quantity region of the detection compartment, so that the at least one first component is completely separated from the at least one second component.

8. The flow-path structure as claimed in claim 7, wherein the first constant-quantity region of the detection compartment comprises a recess.

9. The flow-path structure as claimed in claim 1 further comprising an exhaust compartment, wherein the detection compartment comprises a detecting region and a second constant-quantity region connected between the detecting region and the exhaust compartment.

10. The flow-path structure as claimed in claim 9, wherein second constant-quantity region of the detection compartment comprises a recess.

11. The flow-path structure as claimed in claim 1 further comprising an exhaust compartment connected to the collecting compartment and the detection compartment.

12. The flow-path structure as claimed in claim 1 further comprising a base surface, wherein the plurality of collecting regions of the collecting compartment comprise a first collecting region, a second collecting region and a third collecting region which are formed with different depths from each other, the second collecting region is connected between the first collecting region and the third collecting region, and the second collecting region has a depth ranged between a depth of the first collecting region and a depth of the third collecting region relative to the base surface.

13. The flow-path structure as claimed in claim 12, wherein a sectional difference of the depth of the first collecting region and the depth of the second collecting region is different from a sectional difference of the depth of the second collecting region and the depth of the third collecting region relative to the base surface.

14. The flow-path structure as claimed in claim 12, wherein the collecting compartment further comprises a slanted surface disposed between the first collecting region and the second collecting region relative to the base surface.

15. The flow-path structure as claimed in claim 12, wherein the third collecting region of the collecting compartment comprises a similar L-shaped chamber formed with an opening connected to the second collecting region.

16. The flow-path structure as claimed in claim 1 further comprising a main board comprising a base surface, a buffering compartment, an overflowing compartment connected to the collecting compartment, and an exhaust compartment connected to the detection compartment, wherein the plurality of collecting regions of the collecting compartment comprise a first collecting region, a second collecting region and a third collecting region which are formed with different depths from each other, the second collecting region is connected between the first collecting region and the third collecting region, the buffering compartment connected between the uniform dividing compartment and the collecting compartment relative to the reference position, wherein the uniform dividing compartment, the buffering compartment, the overflowing compartment, the detection compartment, the exhaust compartment, and the first, second and third collecting regions of the collecting compartment are slots formed on the base surface of the main board, and the depth of the second collecting region of the collecting compartment and the depth of the separation channel are relatively less than the depths of the injection compartment, the uniform dividing compartment, the buffering compartment, the overflowing compartment, and the first collecting region and the third collecting region of the collecting compartment.

17. The flow-path structure as claimed in claim 1, wherein the working fluid located in the uniform dividing compartment is transmitted to the collecting compartment at a first predetermined time period when the uniform dividing compartment is rotated relative to the reference position, and the separation of the at least one first and second components of the working fluid located at the plurality of collecting regions of the collecting compartment is performed at a second predetermined time period, wherein the first predetermined time period is prior to the second predetermined time period, and the plurality of collecting regions of the collecting compartment are filled with the separated first component, and wherein the at least one first component of the working fluid located at the plurality of collecting regions of the collecting compartment is transmitted to the separation channel when the rotating uniform dividing compartment is stopped relative to the reference position, and the separated at least one first component located at the separation channel is centrifugally transmitted to the detection compartment through the separation channel by an acting force when the uniform dividing compartment that was stopped begins to rotate relative to the reference position, so that the at least one first component is completely separated from the at least one second component.

18. The flow-path structure as claimed in claim 17, wherein the acting force comprises a Coriolis force generated by Coriolis acceleration.

19. The flow-path structure as claimed in claim 17, wherein the working fluid is moved by an accelerated motion in the first predetermined time period relative to the reference position, and the working fluid is moved by a uniform velocity motion in the second predetermined time period relative to the reference position.

20. The flow-path structure as claimed in claim 1, wherein the uniform dividing compartment and the collecting compartment are arranged along a radial direction relative to the reference position.

21. The flow-path structure as claimed in claim 1, wherein the flow-path structure is rotated about a reference axis at which the reference position is located.

22. The flow-path structure as claimed in claim 1, wherein the separation channel comprises at least one segment connected to at least one of the plurality of collecting regions of the collecting compartment, an oblique angle formed between an extending direction of the at least one segment of the separation channel and an extending direction of the at least one of the plurality of collecting regions of the collecting compartment is not greater than 30 degrees.

23. The flow-path structure as claimed in claim 1, wherein the separation channel comprises a first segment obliquely connected to the at least one of the plurality of collecting regions of the collecting compartment, a second segment, and a third segment connected to the detection compartment, wherein the second segment is connected between the first segment and the third segment, a first angle formed between the first segment and the second segment is not less than 90 degrees, and a second angle formed between the second segment and the third segment is not greater than 90 degrees.

24. The flow-path structure as claimed in claim 1, wherein a specific gravity of the at least one first component is different from that of the at least one second component.

25. An analytical system capable of analyzing a working fluid comprising at least one first component and at least one second component with different characteristics therebetween, comprising:
a uniform dividing unit comprising a plurality of uniform dividing compartments utilized to uniformly divide the working fluid and to be rotated relative to a reference position, each of the plurality of uniform dividing compartments comprising a section gradually reduced away from the reference position;
a separation unit comprising a plurality of collecting compartments respectively connected to the plurality of uniform dividing compartments of the uniform dividing unit and a plurality of separation channels, each of the plurality of collecting compartments comprising a plurality of collecting regions connected to each other; and
a detection unit comprising a plurality of detection compartments respectively connected to at least one of the plurality of collecting regions of each of the plurality of collecting compartments through the plurality of separation channels of the separation unit;
when the plurality of uniform dividing compartments of the uniform dividing unit are rotated relative to the reference position, the working fluid located at the plurality of uniform dividing compartments of the uniform dividing unit is transmitted to the plurality of collecting regions of the plurality of collecting compartments of the separation unit, and the at least one first component and the at least one second component of the working fluid are centrifugally separated from each other by the plurality of collecting regions of the plurality of collecting compartments of the separation unit; and
when the rotating plurality of uniform dividing compartments of the uniform dividing unit are stopped relative to the reference position, the at least one first component of the working fluid located at the plurality of collecting regions of the collecting compartments of the separation unit is transmitted to the separation channels, and when the plurality of uniform dividing compartments of the uniform dividing unit those were stopped begin to rotate relative to the reference position, the at least one first component of the working fluid located at the plurality of separation channels of the separation unit is centrifugally transmitted to the plurality of detection compartments of the detection unit through the plurality of separation channels of the separation unit, so that the at least one first component is completely separated from the at least one second component.

26. The analytical system as claimed in claim 25, wherein the plurality of uniform dividing compartments of the uniform dividing unit comprise a droplet-like hollow structure formed with at least one slanted surface, respectively.

27. The analytical system as claimed in claim 25, wherein the uniform dividing unit further comprises a plurality of buffering compartments respectively connected between the plurality of uniform dividing compartments and the plurality of collecting compartments of the separation unit relative to the reference position, and each of the plurality of buffering compartments comprises a section gradually reduced away from the reference position.

28. The analytical system as claimed in claim 27, wherein the plurality of buffering compartments of the uniform dividing unit comprise a droplet-like hollow structure, respectively.

29. The analytical system as claimed in claim 27, wherein each of the plurality of uniform dividing compartments of the uniform dividing unit, each of the plurality of buffering compartments of the uniform dividing unit, and each of the plurality of collecting compartments of the separation unit are arranged along a radial direction passing through the reference position.

30. The analytical system as claimed in claim 25 further comprising an overflowing unit comprising a plurality of overflowing compartments respectively connected to the plurality of collecting compartments of the separation unit;
when the plurality of overflowing compartments of the overflowing unit are rotated relative to the reference position, excess working fluid injected to the plurality of collecting compartments of the separation unit is transmitted to the plurality of overflowing compartments of the overflowing unit.

31. The analytical system as claimed in claim 25, wherein each of the plurality of detection compartments of the detection unit comprises a detecting region and a first constant-quantity region connected between each of the plurality of separation channels of the separation unit and the detecting region;
when the rotating plurality of uniform dividing compartments of the uniform dividing unit is stopped relative to the reference position, the at least one first component of the working fluid located at the plurality of collecting regions of the collecting compartments of the separation unit is transmitted to the plurality of separation channels of the separation unit, and when the plurality of uniform dividing compartments of the uniform dividing unit those were stopped begin to rotate relative to the reference position, the at least one first component of the working fluid located at the plurality of separation channels of the separation unit is centrifugally transmitted to the detecting regions of the plurality of detection compartments of the detection unit through the plurality of separation channels of the separation unit and the plurality of first constant-quantity regions of the plurality of detection compartments of the detection unit, so that the at least one first component is completely separated from the at least one second component.

32. The analytical system as claimed in claim 31, wherein the plurality of first constant-quantity regions of the plurality of detection compartments of the detection unit comprise a plurality of recesses.

33. The analytical system as claimed in claim 25 further comprising an exhaust unit comprising a plurality of exhaust compartments, wherein each of the plurality of detection compartments of the detection unit comprises a detecting region and a second constant-quantity region connected between the detecting region and each of the plurality of exhaust compartments of the exhaust unit.

34. The analytical system as claimed in claim 33, wherein the plurality of second constant-quantity regions of the plurality of detection compartments of the detection unit comprise a plurality of recesses.

35. The analytical system as claimed in claim 25 further comprising an exhaust unit comprising a plurality of exhaust compartments respectively connected to the plurality of collecting compartments of the separation unit and the plurality of detection compartments of the detection unit.

36. The analytical system as claimed in claim 25 further comprising a main board comprising a base surface, wherein each of the plurality of collecting regions of the plurality of collecting compartments of the separation unit comprise a first collecting region, a second collecting region and a third collecting region which are formed with different depths from each other, the second collecting region is connected between the first collecting region and the third collecting region, and the second collecting region has a depth ranged between a depth of the first collecting region and a depth of the third collecting region relative to the base surface of the main board.

37. The analytical system as claimed in claim 36, wherein a sectional difference of the depth of the first collecting region and the depth of the second collecting region is different from a sectional difference of the depth of the second collecting region and the depth of the third collecting region relative to the base surface of the main board.

38. The analytical system as claimed in claim 36, wherein each of the plurality of collecting compartments of the separation unit further comprises a slanted surface disposed between the first collecting region and the second collecting region relative to the base surface of the main board.

39. The analytical system as claimed in claim 36, wherein each of the plurality of third collecting regions of the plurality of collecting compartments of the separation unit comprises a similar L-shaped chamber formed with an opening connected to the second collecting region.

40. The analytical system as claimed in claim 25 further comprising a main board comprising a base surface, an overflowing unit comprising a plurality of overflowing compartments respectively connected to the plurality of collecting compartments of the separation unit, an exhaust unit comprising a plurality of exhaust compartments respectively connected to the plurality of detection compartments of the detection unit, and an injection unit comprising an injection compartment connected to the plurality of uniform dividing compartments of the uniform dividing unit to receive the working fluid to be injected, wherein the uniform dividing unit further comprises a plurality of buffering compartments, the plurality of collecting regions of each of the plurality of collecting compartments of the separation unit comprise a first collecting region, a second collecting region and a third collecting region which are formed with different depths from each other, the second collecting region is connected between the first collecting region and the third collecting region, the plurality of buffering compartments of the uniform dividing unit are respectively connected between the uniform dividing compartment of the uniform dividing unit and the collecting compartment of the separation unit relative to the reference position, wherein the plurality of uniform dividing compartments and the plurality of buffering compartments of the uniform dividing unit, the plurality of overflowing compartments of the overflowing unit, the plurality of detection compartments of the detection unit, the plurality of exhaust compartments of the exhaust unit, the first, second and third collecting regions of the plurality of collecting compartments of the separation unit are slots formed on the base surface of the main board, and the depths of the plurality of second collecting regions of the plurality of collecting compartments of the separation unit and the depths of the plurality of separation channels of the separation unit are relatively less than the depths of the injection compartment of the injection unit, the plurality of uniform dividing compartments and the plurality of buffering compartments of the uniform dividing unit, the plurality of overflowing compartments of the overflowing unit, and the first and third collecting regions of the plurality of collecting compartments of the separation unit.

41. The analytical system as claimed in claim 25, wherein the working fluid located at the plurality of uniform dividing compartments of the uniform dividing unit is transmitted to the collecting compartment at a first predetermined time period when the plurality of uniform dividing compartments of the uniform dividing unit is rotated relative to the reference position, and the separation of the at least one first and second components of the working fluid located at the plurality of collecting regions of the plurality of collecting compartments of the separation unit is performed at a second predetermined time period, wherein the first predetermined time period is prior to the second predetermined time period, and the plurality of collecting regions of the plurality of collecting compartments of the separation unit are filled with the separated first component and wherein the at least one first component of the working fluid located at the plurality of collecting regions of the plurality of collecting compartments of the separation unit is transmitted to the plurality of separation channels of the separation unit when the rotating plurality of uniform dividing compartments of the uniform dividing unit is stopped relative to the reference position, and the separated at least one first component located at the plurality of separation channels of the separation unit is centrifugally transmitted to the detection compartment through the plurality of separation channels of the separation unit by an acting force when the plurality of uniform dividing compartments of the uniform dividing unit those were stopped begin to rotate relative to the reference position, so that the at least one first component is completely separated from the at least one second component.

42. The analytical system as claimed in claim 41, wherein the acting force comprises a Coriolis force generated by Coriolis acceleration.

43. The analytical system as claimed in claim 41, wherein the working fluid is moved by an accelerated motion in the first predetermined time period relative to the reference position, and the working fluid is moved by a uniform velocity motion in the second predetermined time period relative to the reference position.

44. The analytical system as claimed in claim 25, wherein each of the plurality of uniform dividing compartments of the uniform dividing unit and each of the plurality of collecting compartments of the separation unit are arranged along a radial direction relative to the reference position.

45. The analytical system as claimed in claim 25, wherein the uniform dividing unit and the separation unit are rotated about a reference axis at which the reference position is located.

46. The analytical system as claimed in claim 25, wherein each of the plurality of separation channels of the separation unit comprises at least one segment connected to at least one of the plurality of collecting regions of the plurality of collecting compartments of the separation unit, an oblique angle formed between an extending direction of the at least one segment of the separation channel and an extending direction of the at least one of the plurality of collecting regions of the plurality of collecting compartments of the separation unit is not greater than 30 degrees.

47. The analytical system as claimed in claim 25, wherein each of the plurality of separation channels of the separation unit comprises a first segment obliquely connected to the at least one of the plurality of collecting regions of the plurality of collecting compartments of the separation unit, a second segment, and a third segment connected to the detection compartment, wherein the second segment is connected between the first segment and the third segment, a first angle formed between the first segment and the second segment is not less than 90 degrees, and a second angle formed between the second segment and the third segment is not less than 90 degrees.

48. The analytical system as claimed in claim 25, wherein a specific gravity of the at least one first component is different from that of the at least one second component.

49. The analytical system as claimed in claim 25 further comprising a controlling unit and an injection unit comprising an injection compartment connected to the plurality of uniform dividing compartments of the uniform dividing unit to receive the working fluid to be injected, wherein the working fluid injected into the injection compartment of the injection unit is controlled by the controlling unit.

50. The analytical system as claimed in claim 25 further comprising a plurality of objects with a first marked substance and disposed in the plurality of uniform dividing compartments of the uniform dividing unit, wherein the working fluid further comprises a second marked substance capable of bonding to the first marked substance of the objects.

51. The analytical system as claimed in claim 50, wherein the objects comprise glass balls, magnetic balls or other carriers.

52. The analytical system as claimed in claim 50, wherein the first marked substance comprises a conjunctive DNA or RNA, a protein, a biomarker, an antibody, a cell, or other biomolecular, and the second marked substance comprises a markable complementary DNA or RNA, a substrate, an enzyme, a coenzyme, a complement, an antigen, other cells or biomolecular.

53. An analytical method, comprising the steps of:
providing a working fluid comprising at least one first component and at least one second component with different characteristics;
providing a flow-path structure with an injection compartment, a uniform dividing compartment connected to the injection compartment and formed with a gradually-reduced section, a buffering compartment connected to the uniform dividing compartment and formed with a gradually-reduced section, a collecting compartment connected to the uniform dividing compartment and comprising a plurality of collecting regions which are connected to each other and formed with different depths, a separation channel connected to one of the plurality of collecting regions of the collecting compartment, and a detection compartment connected to the separation channel;
injecting the working fluid into the injection compartment of the flow-path structure;
uniformly dividing the working fluid from the injection compartment by the uniform dividing compartment and the buffering compartment to limit the uniformly divided working fluid from entering the plurality of collecting regions of the collecting compartment;
rotating the flow-path structure to cause the working fluid located in the uniform dividing compartment and the buffering compartment entering the collecting compartment, so that the at least one first component and the at least one second component of the working fluid are centrifugally separated from each other by the plurality of collecting regions of the collecting compartment;
stopping the rotation of the flow-path structure to transmit the at least one first component of the working fluid located at the plurality of collecting regions of the collecting compartment toward the detection compartment through the separation channel; and
driving the flow-path structure that was stopped to rotate for transmitting the separated at least one first component to the detection compartment through the separation channel, so that the at least one first component is completely separated from the at least one second component.

54. The analytical method as claimed in claim 53 further providing the following steps:
providing a plurality of objects with a first marked substance and the working fluid with a second marked substance; and
selectively disposing the plurality of objects with the first marked substance in one of the uniform dividing compartment and the buffering compartment, so that the working fluid injected into the uniform dividing compartment and the buffering compartment is capable of bonding to the first marked substance of the objects.

55. The analytical method as claimed in claim 54, wherein the objects comprise glass balls, magnetic balls or other carriers.

56. The analytical method as claimed in claim 54, wherein the first marked substance comprises a conjunctive DNA or RNA, a protein, a biomarker, an antibody, a cell, or other biomolecular, and the second marked substance comprises a markable complementary DNA or RNA, a substrate, an enzyme, a coenzyme, a complement, an antigen, other cells or biomolecular.

57. The analytical method as claimed in claim 53, wherein a specific gravity of the at least one first component is different from that of the at least one second component.

* * * * *